US009790249B2

United States Patent
Beckham et al.

(10) Patent No.: US 9,790,249 B2
(45) Date of Patent: *Oct. 17, 2017

(54) HYDROXIDE CATALYSTS FOR LIGNIN DEPOLYMERIZATION

(71) Applicant: Alliance for Sustainable Energy, LLC, Golden, CO (US)

(72) Inventors: Gregg T Beckham, Denver, CO (US); Mary J. Biddy, Westminster, CO (US); Jacob S. Kruger, Golden, CO (US); Stephen C. Chmely, Golden, CO (US); Matthew Sturgeon, Arvada, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,920

(22) Filed: Aug. 4, 2015

(65) Prior Publication Data

US 2016/0052949 A1 Feb. 25, 2016

Related U.S. Application Data

(63) Continuation-in-part of application No. 14/047,905, filed on Oct. 7, 2013.

(Continued)

(51) Int. Cl.
*C10G 1/04* (2006.01)
*C07G 1/00* (2011.01)
(Continued)

(52) U.S. Cl.
CPC .............. *C07G 1/00* (2013.01); *B01J 23/007* (2013.01); *B01J 23/755* (2013.01); *B01J 27/236* (2013.01); *B01J 35/002* (2013.01); *B01J 37/0201* (2013.01); *B01J 37/031* (2013.01); *C07C 45/513* (2013.01); *C10G 1/086* (2013.01); *C10G 2300/1014* (2013.01); *Y02P 30/20* (2015.11)

(58) Field of Classification Search
None
See application file for complete search history.

(56) References Cited

U.S. PATENT DOCUMENTS 5,776,424 A 7/1998 Martin et al.
6,656,382 B1 * 12/2003 Kuhlmann ............... B01J 41/10
210/683

(Continued)

FOREIGN PATENT DOCUMENTS

WO WO 2010/089691 A1 8/2010

OTHER PUBLICATIONS

Shen et al., Recovery of lignocelluloses from pre-hydroylsis liquor in the lime kiln of kraft-based dissolving pulp production process by adsorption to lime mud, Bioresource Technology 102, 10035-10039, 2011.*

(Continued)

*Primary Examiner* — Philip Louie
(74) *Attorney, Agent, or Firm* — John C. Stolpa; Michael A. McIntyre

(57) ABSTRACT

Solid base catalysts and their use for the base-catalyzed depolymerization (BCD) of lignin to compounds such as aromatics are presented herein. Exemplary catalysts include layered double hydroxides (LDHs) as recyclable, heterogeneous catalysts for BCD of lignin.

18 Claims, 28 Drawing Sheets

Related U.S. Application Data

(60) Provisional application No. 62/100,435, filed on Jan. 6, 2015, provisional application No. 62/032,817, filed on Aug. 4, 2014, provisional application No. 61/857,964, filed on Jul. 24, 2013, provisional application No. 61/710,240, filed on Oct. 5, 2012.

(51) Int. Cl.

| | |
|---|---|
| B01J 27/236 | (2006.01) |
| C07C 45/51 | (2006.01) |
| B01J 37/03 | (2006.01) |
| B01J 23/00 | (2006.01) |
| B01J 23/755 | (2006.01) |
| B01J 35/00 | (2006.01) |
| B01J 37/02 | (2006.01) |
| C10G 1/08 | (2006.01) |

(56) References Cited

U.S. PATENT DOCUMENTS

| | | | |
|---|---|---|---|
| 2007/0053821 A1* | 3/2007 | Gillman | C01C 1/185 423/396 |
| 2008/0050792 A1 | 2/2008 | Zmierczak et al. | |
| 2008/0300352 A1 | 12/2008 | Schomaker et al. | |
| 2010/0254892 A1 | 10/2010 | Takahashi et al. | |
| 2011/0065814 A1* | 3/2011 | Matson | C01B 3/22 518/702 |
| 2011/0152514 A1 | 6/2011 | Kettling et al. | |
| 2011/0275869 A1 | 11/2011 | Prochazka et al. | |
| 2012/0037486 A1 | 2/2012 | O'Connor et al. | |
| 2012/0116063 A1 | 5/2012 | Jansen et al. | |
| 2012/0302796 A1 | 11/2012 | Dhepe et al. | |
| 2013/0232853 A1 | 9/2013 | Peterson et al. | |
| 2014/0107381 A1 | 4/2014 | Beckham et al. | |
| 2016/0017381 A1 | 1/2016 | Beckham et al. | |

OTHER PUBLICATIONS

Aramendia et al., "Catalytic Transfer Hydrogenation of Citral on Calcined Layered Double Hydroxides", Applied Catalysis A—General, Jan. 2001, vol. 206, No. 1, pp. 95-101.

Azadi et al., "Liquid Fuels, Hydrogen and Chemicals from Lignin: A Critical Review", Renewable and Sustainable Energy Reviews, 2013, vol. 21, pp. 506-523.

Bond et al., "Integrated Catalytic Conversion of γ-Valerolactone to Liquid Alkenes for Transportation Fuels", Science, Feb. 2010, vol. 327, No. 5969, pp. 1110-1114.

Bontchev et al., "Synthesis, Characterization, and Ion Exchange Properties of Hydrotalcite Mg6Al2(OH)16(A)x(A')2-x•4H2O (A, A'=Cl-, Br-, I-, and NO3-, 2≥x≥0) Derivatives", Chemistry of Materials, 2003, vol. 15, pp. 3669-3675.

Bozell et al., "Solvent fractionation of renewable woody feedstocks: Organosolv generation of biorefinery process streams for the production of biobased chemicals", Biomass Bioenergy, 2011, vol. 35, No. 10, pp. 4197-4208.

Choudhary et al., "Solvent-free Selective Oxidation of Benzyl Alcohol and Benzaldehyde by Tert-butyl Hydroperoxide Using MnO-4-exchanged Mg-Al-hydrotalcite Catalysts", Catalysis Letters, Mar. 2003, vol. 86, No. 4, pp. 229-233.

Cunha et al., "Sorption Enhanced Steam Reforming of Ethanol on Hydrotalcite-like Compounds Impregnated with Active Copper", Chemical Engineering Research and Design, Mar. 2013, vol. 91, No. 3, pp. 581-592.

Debecker et al., "Exploring, Tuning and Exploiting the Basicity of Hydrotalcites for Applications in Hetergeneous Catalysis", Chemistry a European Journal, 2009, vol. 15, pp. 3920-3935.

Drago et al., "Catalyzed Decomposition of N2O on Metal Oxide Supports", Applied Catalysis B: Environmental, 1997, vol. 13, pp. 69-79.

Fuchs et al., "Microbial Degradation of Aromatic Compounds—From One Strategy to Four", Nature Reviews Microbiology, Nov. 2011, vol. 9, pp. 803-816.

Furimsky, "Catalytic Hydrodeoxygenation", Applied Catalysis A: General, Jun. 12, 2000, vol. 199, No. 2, pp. 147-190.

Galkin et al., "Mild Heterogeneous Palladium-Catalyzed Cleavage of β-O-4'-Ether Linkages of Lignin Model Compounds and Native Lignin in Air", ChemCatChem, Jan. 2014, vol. 6, No. 1, pp. 179-184.

Ionescu et al., "Epoxidation of Cyclohexene With H2O2 and Acetonitrile Catalyzed by Mg—Al Hydrotalcite and Cobalt Modified Hydrotalcites", Catalysis Letters, 2010, vol. 134, Nos. 3-4, pp. 309-317.

Iyi et al., "Deintercalation of Carbonate Ions from a Hydrotalcite-Like Compound: Enhanced Decarbonation Using Acid-Salt Mixed Solution", Chemistry of Materials, 2004, vol. 16, pp. 2926-2932.

Jyothi et al., "Catalytic Transfer Reduction (CTR) of Alkyl Alkyl, Alkyl Aryl, Cyclic and Unsaturated Ketones Over Calcined Mg—Al Hydrotalcites", Journal of Molecular Cataysis A: Chemical, 2001, vol. 168, pp. 187-191.

Jyothi et al., "Chemoselective Transfer Hydrogenation Reactions over Calcined-Layered Double Hydroxides", The Bulletin of the Chemical Society of Japan, 2000, vol. 73, No. 6, pp. 1425-1427.

Kawabata et al., "Improved Fe/Mg—Al Hydrotalcite Catalyst for Baeyer-Villiger Oxidation of Ketones with Molecular Oxygen and Benzaldehyde", Hournal of Molecular Catalysis A: Chemical, Jul. 2006, vol. 253, Nos. 1-2 pp. 279-289.

Kim et al., "Computational Study of Bond Dissociation Enthalpies for a Large Range of Native and Modified Lignins", The Journal of Physical Chemistry Letters, 2011, vol. 2, No. 22, pp. 2846-2852.

Kooli et al., "FT-IR Spectroscopy Study of Surface Acidity and 2-Propanol Decomposition on Mixed Oxides Obtained upon Calcination of Layered Double Hydroxides", Langmuir, Apr. 1997, vol. 13, No. 8, pp. 2303-2306.

Kurokawa et al., "Solid Base-Catalyzed Reaction of Nitriles with Methanol to Form α,β-unsaturated Nitriles I. Conversion and Selectivity" Journal of Catalysis, Nov. 1990, vol. 126, No. 1, pp. 199-207.

Li et al., "Novel Ru—Mg—Al—O Catalyst Derived from Hydrotalcite-like Compound for NO Storage/Decomposition/Reduction", The Journal of Physical Chemistry C, 2007, vol. 111, pp. 10552-10559.

Li et al., "Regenerability of Hydrotalcite-Derived Nickel-Iron Alloy Nanoparticles for Syngas Production from Biomass Tar", ChemSusChem, Feb. 2014, vol. 7, No. 2, pp. 510-522.

Macala et al., "Hydrogen Transfer from Supercritical Methanol over a Solid Base Catalyst: A model for Lignin Depolymerization", ChemSusChem, 2009, vol. 2, pp. 215-217.

Macala et al., "Transesterification Catalysts from Iron Doped Hydrotalcite-like Precursors: Solid Bases for Biodiesel Production", Catalysis Letters, 2008, vol. 122, pp. 205-209.

Manayil et al., "CoAl—CrO4 Layered Double Hydroxides as Selective Oxidation Catalysts at Room Temperature", Industrial & Engineering Chemistry Research, 2011, vol. 50, pp. 13380-13386.

Matson et al., "One-Pot Catalytic Conversion of Cellulose and of Woody Biomass Solids to Liquid Fuels", Journal of the American Chemical Society, 2011, vol. 133, pp. 14090-14097.

Miyata et al., "Anion-Exchange Properties of Hydrotalcite-Like Compounds", Clays and Clay Minerals, 1983, vol. 31, No. 4, pp. 305-311.

Mohapatra et al., "Reductive Cleavage of Azo Dyes and Reduction of Nitroarenes Over Trivalent Iron Incorporated Hexagonal Mesoporous Aluminophosphate Molecular Sieves", Applied Catalysis B: Environmental, 2003, vol. 46, No. 1, pp. 155-163.

Nalawade et al., "Layered Double Hydroxides: A Review", Journal of Scientific & Industrial Research, Apr. 2009, vol. 68, pp. 267-272.

Nguyen et al., "A Photochemical Strategy for Lignin Degradation at Room Temperature", Journal of the American Chemical Society, 2014, vol. 136, No. 4, pp. 1218-1221.

Onaka et al., "Recent Studies on Solid Acid Catalysis and Solid Base Catalysis for Fine Chemicals Synthesis", Journal of Synthetic Organic Chemistry, Japan, 2005, vol. 63, No. 5, pp. 492-502.

(56) References Cited

OTHER PUBLICATIONS

Pandey et al., "Lignin Depolymerization and Conversion: A Review of Thermochemical Methods", Chemical Engineering & Technology, Jan. 2011, vol. 34, No. 1, pp. 29-41.
Parida et al., "Mg/Al Hydrotalcites: Preparation, Characterisation and Ketonisation of Acetic Acid", Journal of Molecular Catalysis A: Chemical, 2000, vol. 151, pp. 185-192.
Parthasarathi et al., "Theoretical Study of the Remarkably Diverse Linkages in Lignin", The Journal of Physical Chemistry Letters, 2011, vol. 2, No. 20, pp. 2660-2666.
Paul et al., "Mesoporous Nickel-Aluminum Mixed Oxide: A Promising Catalyst in Hydride-Transfer Reactions", European Journal of Inorganic Chemistry, Nov. 2010, vol. 32, pp. 5129-5134.
Pinnavaia et al., "Organic chemical conversions catalyzed by intercalated layered double hydroxides (LDHs)", Applied Clay Science, Aug. 1995, vol. 10, Nos. 1-2, pp. 117-129.
Rahimi et al., "Chemoselective Metal-Free Aerobic Alcohol Oxidation in Lignin", Journal of the American Chemical Society, 2013, vol. 135, No. 17, pp. 6415-6418.
Richardson, "Layered Double Hydoxides as Anion- and Cation-Exchanging Materials", Dissertation Prepared for the Degree of Doctor of Philosophy, University of North Texas, May 2007, pp. 1-197.
Rives et al., "Layered Double Hydroxides (LDH) Intercalated with Metal Coordination Compounds and Oxometalates", Coordination Chemistry Reviews, Jan. 1999, vol. 181, No. 1, pp. 61-120.
Roberts et al., "Towards Quantitative Catalytic Lignin Depolymerization", Chemistry—A European Journal, May 16, 2011, vol. 17, No. 21, pp. 5939-5948.
Schirmer et al., "Microbial Biosynthesis of Alkanes", Science, Jul. 2010, vol. 329, No. 5991, pp. 559-562.
Segal et al., "Catalytic Decomposition of Alcohols, Including Ethanol, for In Situ H2 Generation in a Fuel Stream Using a Layered Double Hydroxide-derived Catalyst", Applied Catalysis A: General, Aug. 2003, vol. 248, Nos. 1-2, pp. 33-45.
Segal et al., "Low Temperature Steam Reforming of Methanol Over Layered Double Hydroxide-derived Catalysts", Applied Catalysis A: General, May 2002, vol. 231, Nos. 1-2, pp. 215-226.
Sharma et al., "Hyrdotalcite Catalysis of Hyrdrotreating Reactions", ACS Spring Meeting Preprints, obtained from http://web.anl.gov/PCS/acsfuel/preprint%20archive/Files/36_2_ATLANTA_04-91_0570.pdf, 1991, pp. 570-577.
Silva et al., "Layered Double Hydroxides as Highly Efficient Photocatalysts for Visible Light Oxygen Generation from Water", Journal of the American Chemical Society, 2009, vol. 131, No. 38, pp. 13833-13839.
Song et al., "Hydrogenolysis of Lignosulfonate into Phenols Over Heterogeneous Nickel Catalysts", Chemical Communications, 2012, vol. 48, pp. 7019-7021.
Song et al., "Lignin Depolymerization (LDP) in Alcohol Over Nickel-based Catalysts via a Fragmentation-hydrogenolysis Process", Energy & Environmental Science, 2013, vol. 6, pp. 994-1007.
Sturgeon et al., "Lignin Depolymerisation by Nickel Supported Layered-double Hydroxide Catalysts", Green Chemistry, 2014, vol. 16, pp. 824-835.
Turco et al., "Production of hydrogen from oxidative steam reforming of methanol: II. Catalytic activity and reaction mechanism on Cu/ZnO/Al2O3 hydrotalcite-derived catalysts", Journal of Catalysis, Nov. 2004, vol. 228, No. 1, pp. 56-65.
Wang et al., "Recent Development in Chemical Depolymerization of Lignin: A Review", Journal of Applied Chemistry, 2013, vol. 2013, pp. 1-9.
Wang et al., "Solvent Effects on the Hydrogenolysis of Diphenyl Ether with Raney Nickel and their Implications for the Conversion of Lignin", ChemSusChem, Aug. 2012, vol. 5, No. 8, pp. 1455-1466.
Xi et al., "Influence of water on the activity and stability of activated Mg—Al Hydrotalcites for the Transesterification of Tributyrin with Methanol", Journal of Catalysis, 2008, vol. 254, No. 2, pp. 190-197.
Zaheer et al., "Robust Heterogeneous Nickel Catalysts with Tailored Porosity for the Selective Hydrogenolysis of Aryl Ethers", ChemCatChem, Jan. 2014, vol. 6, No. 1, pp. 91-95.
Zakzeski et al., "The Catalytic Valorization of Lignin for the Production of Renewable Chemicals", Chemical Reviews, 2010, vol. 110, pp. 3552-3599.
Zumreoglu-Karan et al., "Layered Double Hydroxides—Multifunctional Nanomaterials", Chemical Papers, 2012, vol. 66, No. 1, pp. 1-10.

\* cited by examiner

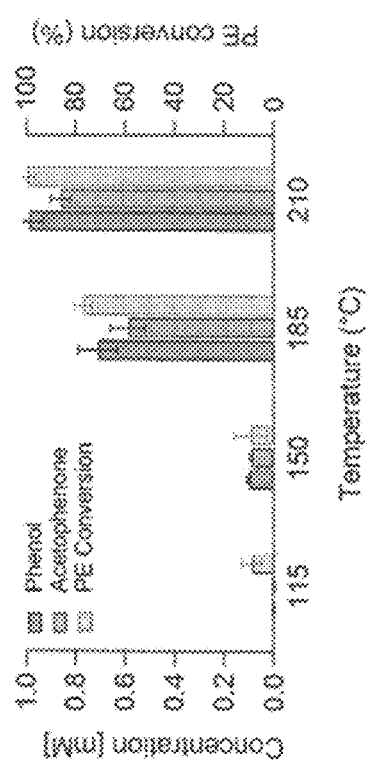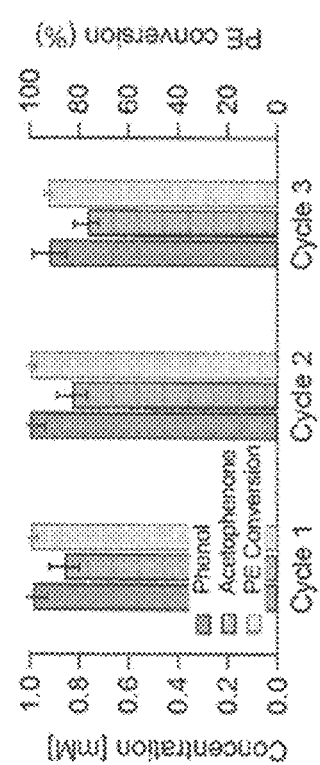
Figure 5A
Figure 5B

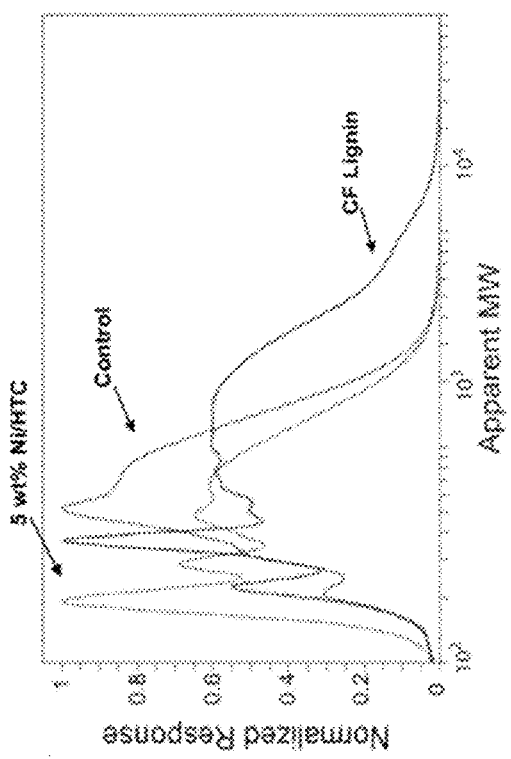
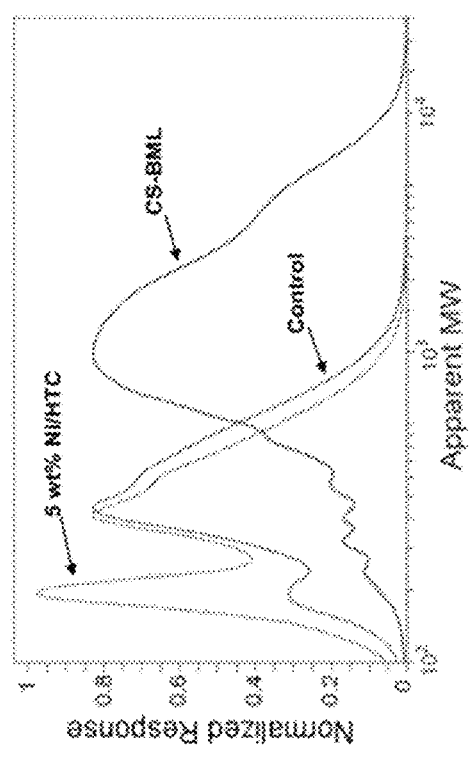
Figure 6A
Figure 6B

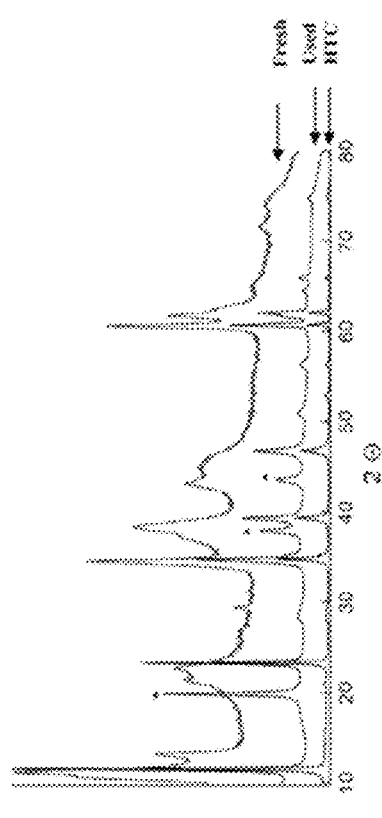
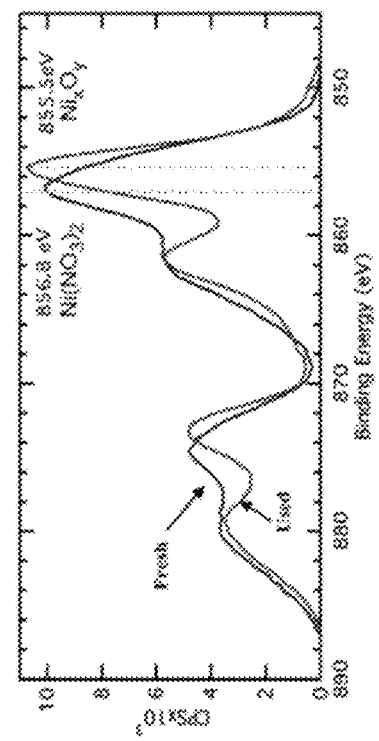
Figure 7A
Figure 7B

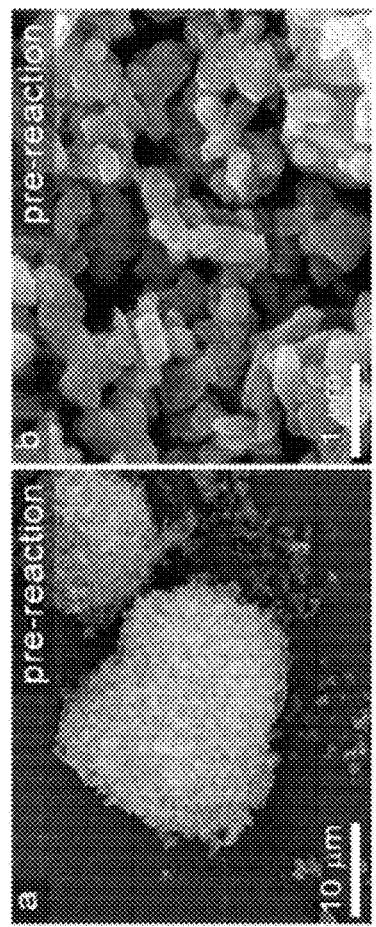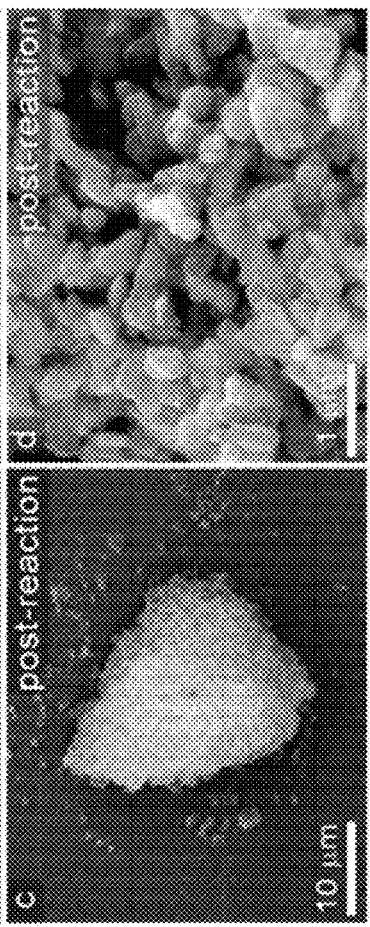

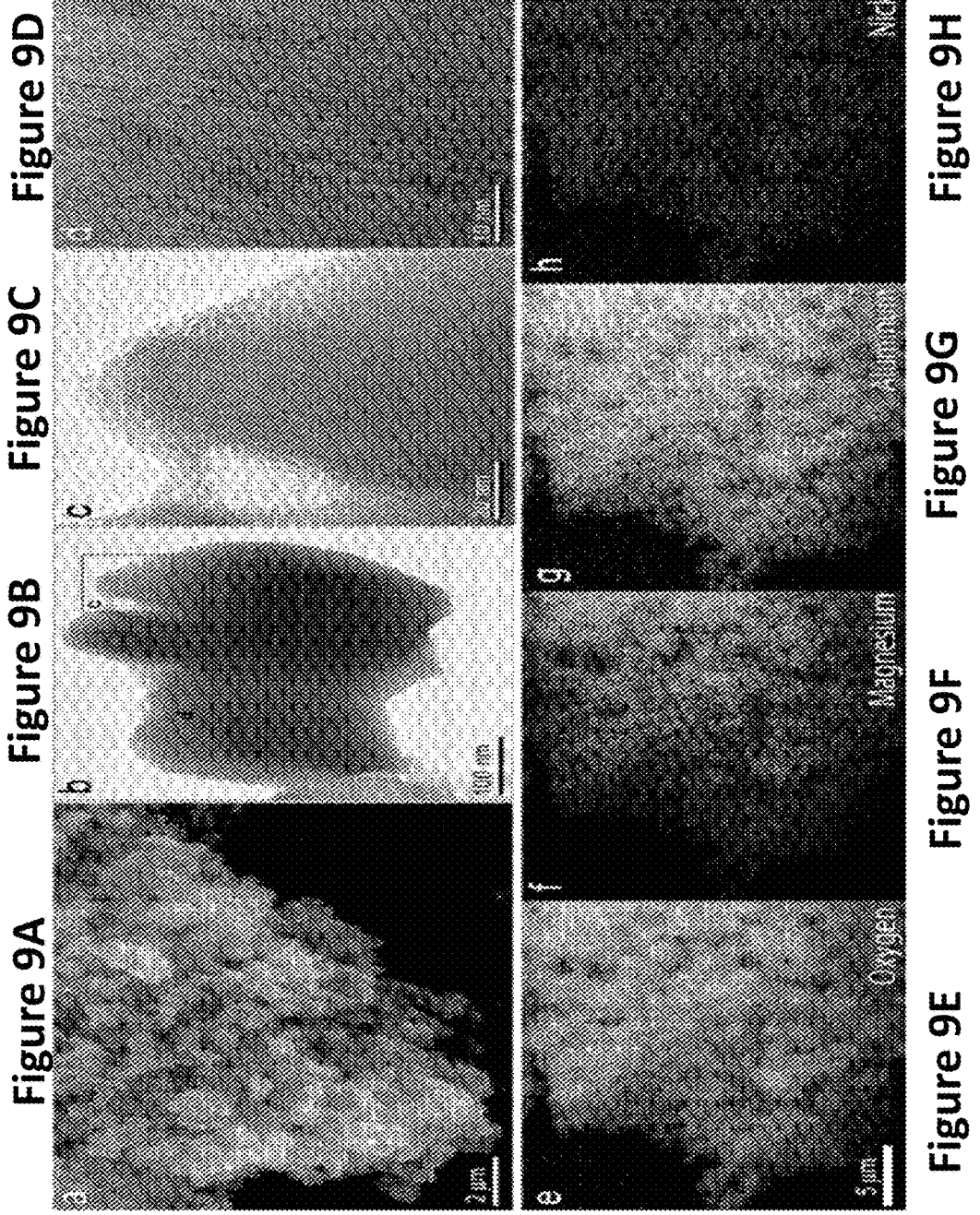

HYDROXIDE CATALYSTS FOR LIGNIN DEPOLYMERIZATION

CROSS-REFERENCE TO RELATED APPLICATIONS

This application is a continuation-in-part of U.S. patent application Ser. No. 14/047,905 filed on Oct. 7, 2013, entitled "HYDROXIDE CATALYSTS FOR LIGNIN DEPOLYMERIZATION", which is incorporated herein by reference in its entirety. This application also claims priority to, and the benefit of, U.S. Provisional Application Nos. 62/032,817 and 62/100,435 filed on Aug. 4, 2014 and Jan. 6, 2015 respectively, both entitled "HYDROXIDE CATALYSTS FOR LIGNIN DEPOLYMERIZATION", both incorporated herein by reference in their entireties.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

BACKGROUND

The production of biofuels and commodity chemicals from lignocellulosic biomass is a major component of the international renewable energy technology portfolio. To date, most research efforts have focused on the cellulose and hemicellulose components of biomass. However, lignin constitutes nearly 30% of woody biomass and represents a rich source of organic macromolecules that can serve as precursors for aromatic and alkane derivatives. Lignin is thus an underutilized value stream in current biomass conversion technologies due to a lack of economic and technically feasible routes for lignin depolymerization and upgrading to fuels.

Lignins can be depolymerized to aromatics with NaOH. In addition, base-catalyzed depolymerization (BCD) has also been applied for lignin deconstruction (e.g., the Kraft process and soda pulping) in the pulp and paper industry with aqueous-phase basic media. To date, efforts in BCD have relied on the use of liquid-phase, homogeneous lignin deconstruction, which requires substantial treatment to neutralize the resulting streams, and thus adds significantly to the cost of lignin deconstruction. However, this is not an economically feasible strategy for biofuels production. Thus, alternative technologies are needed for effective depolymerization of lignin in biomass for subsequent fuel and chemical production.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Provided herein are methods for contacting an aromatic-containing material with a solvent and a catalyst comprising an anion associated with a solid to break at least one bond of the material, creating at least one lower molecular weight product.

In certain embodiments, the aromatic-containing material comprises a lignin-derived compound, such as p-coumaryl alcohol, coniferyl alcohol, or sinapyl alcohol.

In various embodiments, the solvent comprises at least one of water, an alcohol, an alkane or a ketone. Exemplary solvents include water, methanol, ethanol, propanol, isopropanol, acetone, methyl isobutyl ketone, heptane, tert-butanol, 2-ethyl-1-hexanol, or 3-methyl-3-pentanol.

In some embodiments, the solid comprises at least one of a layered double hydroxide (LDH), an aluminosilicate, an alumina, a silica, hydrotalcite or titanium dioxide. The solid may comprise an LDH characterized by $[M^{II}_{1-x}M^{III}_{x}(OH)_2]^{x+}$, such as $Mg_6Al_2(OH)_{16}$.

In certain embodiments, the anion associated with the solid comprises at least one of carbonate, nitrate, nitrite, arsenate, phosphate, arsenite, hydrogen phosphate, dihydrogen phosphate, sulfate, hydrogen sulfate, nitrite, thiosulfate, sulfite, perchlorate, iodate, bromate, chlorite, hypochlorite, hypobromite, chromate, hydrogen carbonate, dichromate, formate, acetate, cyanide, amide, cyanate, peroxide, oxalate, hydroxide, permanganate, hydride, oxide, fluoride sulfide, chloride, nitride, bromide, or iodide.

In some embodiments, the aromatic-containing material contains lignin, and the material is separated from a biomass source comprising lignin, cellulose, and hemicellulose prior to the contacting. The material containing lignin may be separated from the biomass source by the Kraft process.

In various embodiments, the step of contacting the material with the solvent and the catalyst occurs at a temperature ranging from about 150° C. to about 300° C. and/or for a period of time ranging from about 1 minute to about 8 hours.

In some embodiments, an additional step of separating the at least one lower molecular weight product from at least one of the solvent or the catalyst is conducted.

Also provided are methods for depolymerizing lignin in a biomass feedstock by separating a lignin-enriched fraction from the biomass feedstock and then contacting the lignin-enriched fraction with a catalyst comprising a nitrate anion associated with a hydrotalcite solid to depolymerize the lignin in the fraction. The method may also comprise a further step of isolating at least one lignin depolymerization product from the catalyst contacted lignin-enriched fraction.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 2A shows the structure of the model lignin compound 2-phenoxy-1-phenethanol (PE), while

FIGS. 5A and 5B show temperature effects on catalytic conversion of PE (A) and the results of recycling studies (B), according to exemplary embodiments of the present invention.

FIGS. 6A and 6B show gel permeation chromatography (GPC) data from the catalytic degradation of lignin from an Organosolv process (CF lignin) in MIBK (A) and of ball-milled lignin (CS-BML) in water (B), according to exemplary embodiments of the present invention.

FIGS. 7A and 7B show the results of X-ray diffraction (A) and X-ray photoelectron spectroscopy (B) analyses of fresh and used 5 wt % Ni/HTC catalyst, according to exemplary embodiments of the present invention.

FIGS. 8A-D show scanning electron microscopy images of catalyst particles pre-reaction (Figures A and B) and post-reaction (Figures C and D), according to exemplary embodiments of the present invention.

FIGS. 9A-H show scanning electron microscopy images (Figure A), transmission electron microscopy images (Figures B-D) and energy dispersive X-ray spectroscopy images (Figures E-H) of 5 wt % Ni/HTC catalyst particles, according to exemplary embodiments of the present invention.

REFERENCE NUMBERS

Figure 1A:
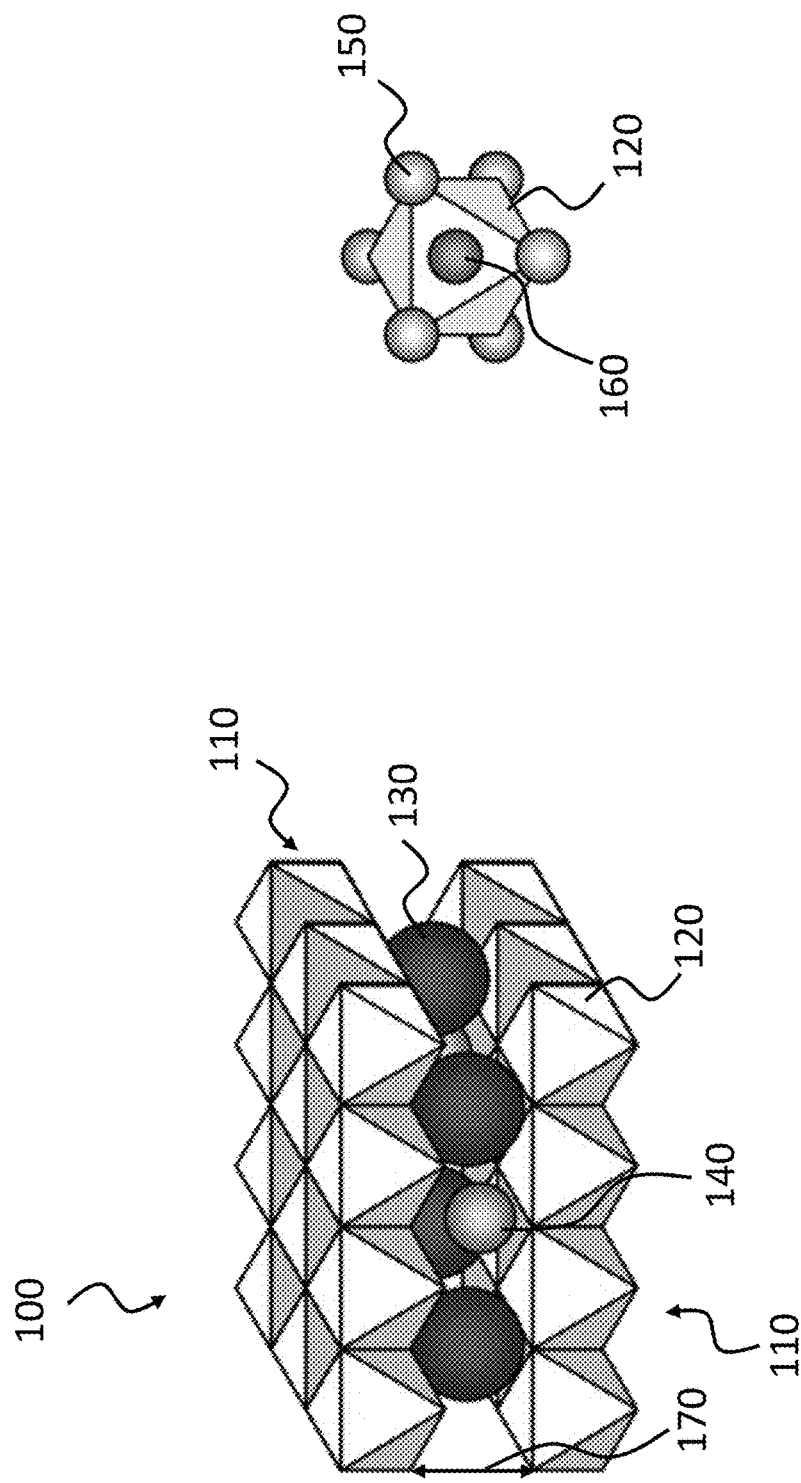
FIG. 1A shows a diagram of an exemplary layered double hydroxide (LDH), according to exemplary embodiments of the present invention.

100 . . . layered double hydroxide (LDH)
110 . . . hydroxide layer
120 . . . subunit
130 . . . $A^{n-}$ anion
140 . . . water
150 . . . hydroxide anion
160 . . . metal cation
170 . . . space
180 . . . separation of lignin material from biomass
185 . . . depolymerization of lignin
190 . . . separation/purification of lignin depolymerization products
200 . . . 2-phenoxy-1-phenethanol (PE)
210 . . . phenol
220 . . . acetophenone
230 . . . β-O-4 bond

DETAILED DESCRIPTION

Solid base catalysts and their use for the base-catalyzed depolymerization (BCD) of lignin to compounds such as aromatics are presented herein. Such solid base catalysts avoid the cost of liquid-phase, non-recyclable base, and downstream processing steps such as neutralization. Exemplary catalysts include layered double hydroxides (LDHs) as recyclable, heterogeneous catalysts for BCD of lignin. Layered double hydroxides presented herein can act as solid base catalysts, and are stable in water and organic solvents at relatively high working temperatures. Examples of LDHs utilized for base-catalyzed depolymerization are provided in Patent Application Publication No. 2014/0107381, which is incorporated herein by reference in its entirety.

Lignin is a heterogeneous alkyl-aromatic polymer that can comprise up to 30-40% of the plant cell wall by mass, depending on the plant type. During cell wall biosynthesis, it is thought that lignin is polymerized via radical coupling reactions from three monomeric units: p-coumaryl alcohol (H), coniferyl alcohol (G), and sinapyl alcohol (S), which exhibit different degrees of ring methoxy-substituents. The presence of these monomers with variable molecular connectivity imparts an inherently heterogeneous structure to lignin, resulting in a variety of C—O and C—C intermonomer bonds with varying reactivity and bond strengths. Due to its heterogeneous structure and reactivity, production of fuels and chemicals from lignin has been technically challenging relative to carbohydrate utilization to date. As such, most conversion processes to produce fuels and chemicals from lignocellulosic biomass typically utilize the residual lignin component for combustion to produce process heat and power. A primary technical hurdle in lignin utilization stems from the need to develop robust catalysts for lignin depolymerization to low molecular weight species that can be fractionated and catalytically upgraded.

Catalyst supports that exhibit alkaline character may be employed here as a starting point for catalyst design, for example, layered double hydroxides (LDHs). LDHs are ionic, lamellar materials with positively charged, hydroxide layers and interstitial anions, and may be described by the general formula:

$$[M^{II}_{1-x}M^{III}_{x}(OH)_2]^{x+}[A^{n-}_{x/n}\cdot yH_2O]^{x-}$$ (Formula 1)

Referring to FIG. 1A, a layered double hydroxide solid 100 may include parallel hydroxide layers 110, where each hydroxide layer 110 is constructed from a plurality of subunits 120, where each subunit 120 is constructed from a metal cation 160 and hydroxide anions 150 (where hydroxide refers to OH$^-$). As shown in FIG. 1A, a subunit 120 may be in the form of an octahedron. The metal cation 160 may be a divalent metal cation ($M^{II}$) or a trivalent metal cation ($M^{III}$), respectively. Opposing hydroxide layers 110 may form a space 170 that allows $A^{n-}$ anions 130 and water 140 to intercalate into the space 170 between the opposing hydroxide layers 110. $A^{n-}$ anions 130 may be n-valent anions, where x may range from 0 to 1.0 or from about 0.25 to about 0.33. The space 167 between the opposing hydroxide layers 110 of the LDH 100 may provide catalytic sites for lignin depolymerization reactions to occur.

As shown in FIG. 1A, LDHs may be constructed to form metal hydroxides. However, an LDH may include a single metal compound such as brucite, where the term "brucite" refers to a layered, lamellar material comprising the single metal compound $Mg(OH)_2$. Thus, LDHs offer significant breadth of available chemistries as both the metals in brucite-like layers and the anions in the interstitial layers may be tuned to meet specific design criteria. As a result, LDHs may be used either directly as catalysts or as active supports in multifunctional catalysts, and LDHs possess a range of possible substrates because of the tunability of the interlayer spacing and the ability to select different intercalating $A^{n-}$ anions 130 positioned within the space 170. Hydrotalcite (HTC), $Mg_6Al_2(OH)_{16}(CO_3)\cdot 4H_2O$, represents a specific example of LDH that exhibits a well-defined structure similar to that shown in FIG. 1A. Thus, as used herein, "LDH catalysts" refers to catalysts that use LDHs directly as catalyst and catalysts that use LDHs as solid supports for other catalytically active elements (e.g. atoms, molecules, species, etc.).

LDH catalysts may include a salt of a divalent metal ion component ($M^{II}$). Examples include chlorides or nitrates of first row transition metals. Examples of divalent metal ion components ($M^{II}$) include at least one of magnesium (Mg), nickel (Ni), iron (Fe), cobalt (Co), copper (Cu), zinc (Zn), calcium (Ca), tin (Sn), barium (Ba), chromium (Cr), strontium (Sr), manganese (Mn), and/or lead (Pb).

LDH catalysts may also include a trivalent metal ion component ($M^{III}$) that may be present in a desired ratio in relation to the divalent metal ion component ($M^{II}$). Examples of trivalent metal components ($M^{III}$) include at least one of aluminum (Al), scandium (Sc), gallium (Ga), bismuth (Bi), nitrogen (N), iron (Fe), chromium (Cr), manganese (Mn), phosphorous (P), and/or indium (In). The ratio of a divalent metal component to a trivalent metal component may range from 1:2 to 10:1, such as 1:2, 1:1, 2:1, 3:1, 4:1, 5:1, 6:1, 7:1, 8:1, 9:1, 10:1 or any fractional value within these ranges.

In addition, an LDH catalyst may comprise a monovalent metal ion component ($M^{I}$) that is in a particular ratio with a trivalent metal ion component ($M^{III}$).) Examples of monovalent metal ion components ($M^{I}$) include at least one of lithium (Li), sodium (Na), potassium (K), rubidium (Rb), cesium (Cs), francium (Fr), silver (Ag), copper (Cu), and/or gold (Au). The ratio of a monovalent metal ion component ($M^{I}$) to a trivalent metal ion component ($M^{III}$) may vary from 1:1 to 10:1, such as 2:1, 3:1, 4:1, 5:1, 6:1, 7:1, 8:1, 9:1 or any fractional value within these ranges.

An LDH catalyst may include at least one monovalent metal ion component ($M^{I}$), divalent metal ion component ($M^{II}$), and/or trivalent metal ion component ($M^{III}$).) For example, an LDH catalyst may include at least one monovalent metal ion component and at least one divalent metal ion component, or at least one monovalent metal ion component and at least one trivalent metal ion component, or at least one divalent metal ion component and at least one trivalent metal ion component. In some examples, an LDH may include at least one monovalent metal ion component, or at least one divalent metal ion component, or at least one trivalent metal ion component.

An LDH catalyst for lignin depolymerization may include an LDH and a metal salt that may be associated with the LDH, for example, wherein the metal salt may be positioned substantially within the space 170 between opposing hydroxide layers 110 of the LDH 100 (see FIG. 1A; metal salt not shown). As used herein, the term "metal salt" refers to a metal counter ion that may be ionically bound to an anion ($A^{n-}$) to counter-balance the negative charge of the anion ($A^{n-}$), where $A^{n-}$ may be associated with the LDH as shown in Formula 1 and FIG. 1A (metal counter ion not shown in either Formula 1 or FIG. 1). Examples of a metal counter ion include at least one of magnesium (Mg), nickel (Ni), iron (Fe), cobalt (Co), copper (Cu), zinc (Zn), calcium (Ca), tin (Sn), barium (Ba), chromium (Cr), strontium (Sr), manganese (Mn), lead (Pb), aluminum (Al), scandium (Sc), gallium (Ga), bismuth (Bi), nitrogen (N), iron (Fe), chromium (Cr), manganese (Mn), phosphorous (P), indium (In), lithium (Li), sodium (Na), potassium (K), rubidium (Rb), cesium (Cs), francium (Fr), silver (Ag), copper (Cu), gold (Au), and/or vanadium (V).

However, in other examples an anion ($A^{n-}$) may not be ionically bound to a metal counter ion. In other words, an anion ($A^{n-}$) may not be ionically associated with a metal counter ion to form a metal salt positioned within the space between opposing hydroxide layers of an LDH catalyst.

In some cases, an LDH catalyst may include an anion ($A^{n-}$), either by itself and/or associated with a metal counter ion, where the anion ($A^{n-}$) may include at least one of carbonate, nitrate, arsenate, phosphate, arsenite, hydrogen phosphate, dihydrogen phosphate, sulfate, hydrogen sulfate, nitrite, thiosulfate, sulfite, perchlorate, iodate, bromate, chlorite, hypochlorite, hypobromite, chromate, hydrogen carbonate, dichromate, formate, acetate, cyanide, amide, cyanate, peroxide, oxalate, hydroxide, permanganate, hydride, oxide, fluoride sulfide, chloride, nitride, bromide, and/or iodide. Examples of metal salts constructed from at least one anion ($A^{n-}$) and at least one metal counter ion include at least one of nickel nitrate, sodium nitrate, magnesium nitrate, iron nitrate, cobalt nitrate, copper nitrate, zinc nitrate, calcium nitrate, tin nitrate, barium nitrate, chromium nitrate, gallium nitrate, and/or vanadium nitrate. In some examples, a metal salt associated with an LDH may include at least one of nickel nitrate, gallium nitrate, zinc nitrate, copper nitrate, cobalt nitrate, chromium nitrate, and/or vanadium nitrate. Still further examples of metal salts that may be associated with an LDH catalyst include at least one of nickel hydroxide, sodium hydroxide, magnesium hydroxide, iron hydroxide, cobalt hydroxide, copper hydroxide, zinc hydroxide, calcium hydroxide, tin hydroxide, barium hydroxide, chromium hydroxide, gallium hydroxide, and/or vanadium hydroxide. A metal counter ion of a metal salt may be in any allowable oxidation state to balance the charge of its corresponding anion ($A^{n-}$). In addition, a metal salt may be hydrated.

Still further examples of a metal salt that may be associated with an LDH catalyst include at least one of nickel chloride, sodium chloride, magnesium chloride, iron chloride, cobalt chloride, copper chloride, zinc chloride, calcium chloride, tin chloride, barium chloride, chromium chloride, gallium chloride, and/or vanadium chloride. A metal salt associated with an LDH catalyst may be at least one of nickel sulfate, sodium sulfate, magnesium sulfate, iron sulfate, cobalt sulfate, copper sulfate, zinc sulfate, calcium sulfate, tin sulfate, barium sulfate, chromium sulfate, gallium sulfate, and/or vanadium sulfate. A metal salt associated with an LDH catalyst may be at least one of nickel carbonate, sodium carbonate, magnesium carbonate, iron carbonate, cobalt carbonate, copper carbonate, zinc carbonate, calcium carbonate, tin carbonate, barium carbonate, chromium carbonate, gallium carbonate, and/or vanadium carbonate. A metal salt associated with an LDH catalyst may be at least one of nickel formate, sodium formate, magnesium formate, iron formate, cobalt formate, copper formate, zinc formate, calcium formate, tin formate, barium formate, chromium formate, gallium formate, and/or vanadium formate. A metal salt associated with an LDH catalyst may be at least one of nickel acetate, sodium acetate, magnesium acetate, iron acetate, cobalt acetate, copper acetate, zinc acetate, calcium acetate, tin acetate, barium acetate, chromium acetate, gallium acetate, and/or vanadium acetate. The metal counter ion of a metal salt may be in any allowable oxidation state to balance the charge of its corresponding anion ($A^{n-}$). In addition, a metal salt may be hydrated.

As used herein, the term "associated" refers to a relationship between at least two components that is at least one of covalent bonding, ionic bonding, hydrogen bonding, van der Waals' forces, pi-effects, hydrophobic interactions, dipole-dipole interactions, London dispersion forces, and/or other electrostatic interactions. Therefore, as used herein, a metal salt that is associated with an LDH is bound to the LDH by at least one of covalent bonding, ionic bonding, hydrogen bonding, van der Waals' forces, pi-effects, hydrophobic interactions, dipole-dipole interactions, London dispersion forces, and/or other electrostatic interactions. Further, the metal counter ion of a metal salt associated with an LDH, or the anion ($A^{n-}$) of the metal salt, or both, may be bound to the LDH by at least one of covalent bonding, ionic bonding, hydrogen bonding, van der Waals' forces, pi-effects, hydrophobic interactions, dipole-dipole interactions, London dispersion forces, and/or other electrostatic interactions. For example, the anion ($A^{n-}$) of a metal salt, for example nitrate, associated with an LDH, and/or the metal counter ion of the metal salt (e.g. nickel), or both, may be associated with the LDH by at least one of covalent bonding, ionic bonding, hydrogen bonding, van der Waals' forces, pi-effects, hydrophobic interactions, dipole-dipole interactions, London dispersion forces, and/or other electrostatic interactions.

A lignin depolymerization catalyst may include an LDH with an anion ($A^{n-}$) associated with the LDH, in the absence of metal counter ion. An LDH catalyst for lignin depolymerization may include, in the absence of a metal counter ion, at least one anion ($A^{n-}$) such as carbonate, nitrate, arsenate, phosphate, arsenite, hydrogen phosphate, dihydrogen phosphate, sulfate, hydrogen sulfate, nitrite, thiosulfate, sulfite, perchlorate, iodate, bromate, chlorite, hypochlorite, hypobromite, chromate, hydrogen carbonate, dichromate, formate, acetate, cyanide, amide, cyanate, peroxide, oxalate, hydroxide, permanganate, hydride, oxide, fluoride sulfide, chloride, nitride, bromide, and/or iodide. For example, a lignin depolymerization catalyst may include an LDH with a nitrate associated with the LDH, in the absence of a metal counter ion. A nitrate may be associated with an LDH by at least one of covalent bonding, ionic bonding, hydrogen bonding, van der Waals' forces, pi-effects, hydrophobic interactions, dipole-dipole interactions, London dispersion forces, and/or other electrostatic interactions. In some cases, an anion ($A^{n-}$) (e.g. nitrate) may be associated with an LDH by electrostatic forces, where there is no corresponding metal counter ion associated with the LDH.

In some examples, the metal of a metal salt may be associated with a surface of an LDH. For example, at least one metal salt may disassociate such that both a metal counter ion and an anion ($A^{n-}$) of the original metal salt may be associated in ionic form with at least one surface of an LDH. Alternatively, at least one metal salt may not disassociate such that both the metal and the anion of the metal salt remain ionically bound to each other, while the metal salt itself may be associated with the LDH.

In addition, the metal counter ion of a metal salt may exchange with at least some of the atoms present in an LDH framework, such that the metal counter ion may be covalently bound within the framework of the LDH. For example, the metal counter ion of a metal salt may exchange with at least one of the magnesium atoms, aluminum atoms, or both of a hydrotalcite. In some cases, the metal counter ion of a metal salt may be nickel, wherein the nickel exchanges with some of the magnesium atoms in the framework of an LDH such as hydrotalcite. In addition, a metal not associated with a metal salt may exchange with the metal cations 160 of a layered double hydroxide 100 (see FIG. 1A).

In some cases, reactions may convert a metal salt to some other species that subsequently associate with an LDH to form a lignin depolymerization catalyst. For example, at least some of a metal salt may be converted to a metal hydroxide, which associates with an LDH to form a lignin depolymerization LDH catalyst. For example, at least a portion of a nickel nitrate associated with an LDH may be converted to a nickel hydroxide. Further, a first portion of the nickel hydroxide may remain such that the nickel and the hydroxide are ionically bound together, and a second portion of the nickel hydroxide may disassociate to form nickel cations and hydroxide anions, wherein the nickel cations and hydroxide anions are electrostatically bound to the LDH.

A layered double hydroxide, such as hydrotalcite (HTC), may be used as a support material to harbor hydroxide anions in the brucite-like layers, which may participate as a catalytic species. An exemplary catalyst is a 5 wt % Ni/HTC catalyst, which is particularly effective at C—O bond cleavage of a model dimer at 270° C. without nickel reduction, where Ni/HTC refers to a catalyst that includes HTC as the LDH, wherein nickel is associated with the HTC. This exemplary 5% Ni/HTC catalyst is able to depolymerize biomass-derived lignin, such as Organosolv lignin. Although nickel is given as an example, one or more other metals as disclosed herein may also be used. In addition, other metals provided on other solid-basic supports (other than an LDH) may function as effective lignin depolymerization catalysts.

The amount of a metal, for example nickel provided to a solid support such as an LDH, utilizing a nickel salt, may be varied depending on the metal used and the desired catalyst properties. Exemplary metal percentages by weight may range from about 1 wt % to 50 wt %, such as about 1, 2, 3, 4, 5, 6, 7, 8, 9, 10, 11, 12, 13, 14, 15, 16, 17, 18, 19, 20, 25, 30, 35, 40, 45 or 50 wt %, as well as values between these integers. For example, an LDH lignin depolymerization catalyst may have a weight percentage of nickel that ranges from about 1 wt % Ni/HTC to about 50 wt % Ni/HTC. For example, nickel may be combined with hydrotalcite in amounts ranging from about 1 wt % Ni/HTC to about 25 wt % Ni/HTC, or from about 5 wt % Ni/HTC to about 15 wt % Ni/HTC. Although nickel is given as an example, other metals as disclosed herein may also be used. As used herein, weight percent (e.g. 5 wt % Ni/HTC) is calculated as the weight of the metal, without a counter balancing anion ($A^{n-}$), divided by the weight of the HTC on a dry basis. The catalyst is defined as "dry" by the final equilibrium weight attained by the catalyst when exposed to ambient, atmospheric conditions (e.g. ambient temperature, humidity, and one atmosphere of pressure).

LDH catalysts for lignin depolymerization may be synthesized by mixing a water-soluble metal salt (e.g., halide or nitrate salt) for each of the metal cations 160 (e.g. divalent $M^{II}$ and trivalent $M^{III}$ metal ion components) in water, adjusting the pH to about 10 or higher, and mixing for 10 minutes to 15 hours. Isolation by filtration or centrifugation, washing of the isolated material, and drying may yield a mixed-metal hydroxy carbonate hydrate material. Optional further treatment of this material by calcination (e.g., at 350-400° C. for one to four hours) may yield a porous metal oxide (PMO) species. Additional details on catalyst synthesis and characterization are provided in the Examples below.

In some examples, a lignin depolymerization catalyst may be constructed using a solid support other than an LDH. For example, a lignin depolymerization catalyst may utilize at least one of a polyoxometalate, a zeolite, an aluminosilicate, a clay, an activated carbon, an alumina, a silica, titanium dioxide or other oxides (e.g., cerium oxide, lanthanum oxide, magnesium oxide, zirconium oxide, or iron oxide), and/or carbides, nitrides, and phosphides (e.g., silicon carbide, tungsten carbide, molybdenum carbide, iron carbide, molybdenum nitride, silicon nitride, tungsten nitride, nickel carbide, nickel phosphide, or tungsten phosphide). Such materials may be used themselves as catalysts for lignin depolymerization reactions, and/or they may be used as solid supports for other active components (e.g. atoms, molecules, ligands, etc.) that catalyze lignin depolymerization reactions. As used herein, the term "aluminosilicate" refers to materials comprising aluminum, silicon, and oxygen. Examples of aluminosilicates include clay minerals and zeolites. Examples of clay minerals include kaolin, smictite, illite, chlorite, sepiolite, and attapulgite. As used herein, a zeolite is a microporous crystalline aluminosilicate, composed of $TO_4$ tetrahedra, wherein "T" is a silicon and/or aluminum atom, with oxygen atoms connecting neighboring tetrahedral. For example, suitable solid catalyst for catalyzing the depolymerization of lignin to lignin-derived aromatic intermediates may include nitrate associated with at least one of an LDH, an aluminosilicate, a polyoxometalate, an activated carbon, a silica, and/or titanium dioxide.

The lignin depolymerization catalysts described herein may be used to deconstruct lignin model compounds, lignin from raw biomass, or lignin-enriched fractions of biomass. One example is biomass subjected to an Organosolv biomass fractionation process (e.g., clean fractionation). Biomass subjected to this process is divided into cellulose, hemicelluloses and lignin fractions, each of which may be further processed for fuel or chemical production. Thus, the catalysts described herein may be incorporated as part of an integrated biorefinery, wherein biomass is first fractionated into streams, and the resulting lignin stream is catalytically depolymerized to create lignin-based aromatic intermediates, which are subsequently reacted to yield useful fuels and/or chemicals.

A lignin depolymerization catalyst, as described herein, may be combined with a solvent, whereby the solvent may promote the disassociation of a metal salt to form metal counter ions (e.g. cations) and anions ($A^{n-}$ per Formula 1 above). Metal counter ions and anions ($A^{n-}$) and/or the solvent may intercalate into the space 170 formed by the hydroxide layers 110 of the layered double hydroxide 100 (see FIG. 1A). Examples of suitable solvents include at least one of water, an alcohol, and/or a ketone. Further examples of suitable solvents include at least one of methanol, ethanol, propanol, isopropanol, acetone, methyl isobutyl ketone (MIBK), 2-ethyl-1-hexanol, and/or 3-methyl-3-pentanol.

In some embodiments of the present invention, a lignin depolymerization catalyst (e.g. an LDH) may be characterized by a BET surface area ranging from about 1.0 $m^2/g$ to about 500 $m^2/g$. Alternatively, a lignin depolymerization catalyst may be characterized by a BET surface area ranging from about 8 $m^2/g$ to about 250 $m^2/g$. In still further examples, a lignin depolymerization catalyst may be characterized by a BET surface area of about 10 $m^2/g$, about 20 $m^2/g$, about 30 $m^2/g$, about 40 $m^2/g$, about 50 $m^2/g$, about 60 $m^2/g$, about 70 $m^2/g$, about 80 $m^2/g$, about 90 $m^2/g$, about 100 $m^2/g$, about 110 $m^2/g$, about 120 $m^2/g$, about 130 $m^2/g$, about 140 $m^2/g$, or about 150 $m^2/g$.

A lignin depolymerization catalyst (e.g. an LDH) may be characterized by a concentration of basic sites ranging from about substantially zero mmol hydroxide anions in the interlayer space per gram of solid catalyst on a wet basis to about 10.0 mmol hydroxide anions per gram of solid catalyst on a wet basis. Alternatively, a lignin depolymerization catalyst may be characterized by a concentration of basic sites ranging from about 0.1 mmol hydroxide anions in the interlayer space per gram of solid catalyst on a wet basis to about 5 mmol hydroxide anions per gram of solid catalyst on a wet basis. In still further examples, a lignin depolymerization catalyst may be characterized by a concentration of basic sites of about 0.1 mmol, about 0.2 mmol, about 0.3 mmol, about 0.4 mmol, about 0.5 mmol, about 0.6 mmol, about 0.7 mmol, about 0.8 mmol, about 0.9 mmol, about 1.0 mmol, about 1.1 mmol, about 1.2 mmol, about 1.3 mmol, about 1.4 mmol, about 1.5 mmol, about 1.6 mmol, about 1.7 mmol, about 1.8 mmol, about 1.9 mmol, or about 2.0 mmol hydroxide anions per gram of solid catalyst on a wet basis.

A solid catalyst for lignin depolymerization (e.g. and LDH) may be substantially crystalline. Alternatively, a solid catalyst for lignin depolymerization may be substantially amorphous. In further examples, a solid catalyst for lignin depolymerization may be partially crystalline and partially amorphous. For example, a solid catalyst for lignin depolymerization may include an LDH that is about 0 wt %, about 10 wt %, about 20 wt %, about 30 wt %, about 40 wt %, about 50 wt %, about 60 wt %, about 70 wt %, about 80 wt %, about 90 wt %, or about 100 wt % crystalline. In other examples, a solid catalyst for lignin depolymerization may include an LDH that is about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, or about 20 wt % crystalline. In still further examples, a solid catalyst for lignin depolymerization may include an LDH that is about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, or about 20 wt % amorphous.

Methods for degrading lignin are also described herein. As used herein, degrading, deconstructing or depolymerizing are synonymous terms for breaking complex lignin polymers down into more basic polymeric or monomeric compounds such as alkanes and/or aromatic compounds. In some embodiments, these lower molecular weight compounds may be isolated and further purified or processed.

Figure 1B:
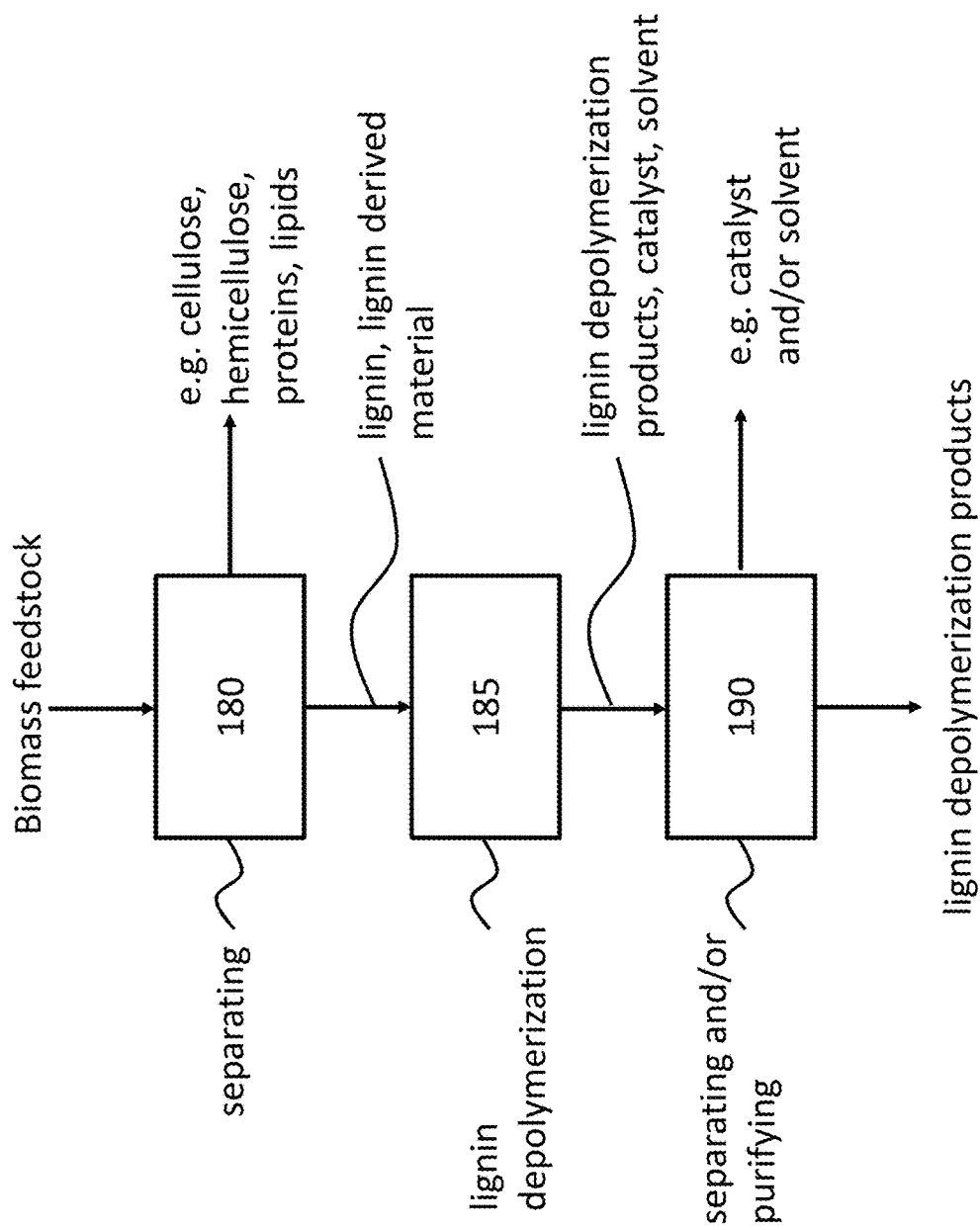
FIG. 1B illustrates an exemplary integrated method for processing biomass to enrich for lignin, depolymerizing the enriched lignin, and then isolating or purifying lignin depolymerization products.

As shown in FIG. 1B, a biomass feedstock may be treated via step 180 to produce lignin or a lignin-enriched stream or fraction for subsequent depolymerization. In general, the cellulose, hemicellulose, protein, lipid and other non-lignin components of biomass may be separated from the lignin to produce the lignin-enriched fraction. The lignin or lignin-enriched fraction may then be subjected to a lignin depolymerization step 185 as described in detail herein. Finally, lignin depolymerization products may be isolated from the depolymerization reaction by a separation or purification step 190.

The lignin feedstock may be prepared from biomass by any number of methods, for example, a chemical method such as the Kraft pulping process, an Organosolv process, a dilute acid pretreatment process, an alkaline pretreatment process, or an enzymatic hydrolysis process. The lignin may also be prepared by a physical method, such as a ball milling process, a disk refining process, a steam explosion process, an ammonia fiber expansion process, or a knife milling process. Alternatively, the lignin may be prepared by combined methods, such as dilute acid pretreatment-enzymatic hydrolysis (DAP lignin), deacetylation-disk refining-enzymatic hydrolysis (DDE lignin). The lignin may come from any type of biomass feedstock, for example, corn stover, switchgrass, or other grassy feedstocks, or from aspen, oak, pine, spruce, or other woody feedstocks. Lignin separation methods can be found in Zakzeski et al., *Chem Rev,* 2010, 110, 3552-3599.

Lignin may be degraded by contacting a lignin-containing material with an LDH catalyst as described herein at a temperature and for a time sufficient to degrade the lignin. In certain embodiments, the lignin and catalyst are contacted in an aqueous solvent such as water or in an organic solvent. Exemplary organic solvents include alcohols such as methanol, ethanol, propanol, isopropanol, 2-ethyl-1-hexanol, and/or 3-methyl-3-pentanol. Other solvents include ketones such as acetone and/or methyl isobutyl ketone (MIBK). In certain cases, the solvent may be water. The step of contacting the lignin with the catalyst may be performed in any reaction vessel or chamber suitable for digestion of biomass or base catalyzed degradation of lignin.

Methods for depolymerizing lignin may include contacting lignin with a solid catalyst (e.g. an LDH) for several minutes, hours or days. Exemplary times include at least 5 minutes, 10 minutes, 15 minutes, 20 minutes, 30 minutes, 45 minutes or 60 minutes; or at least 1 hour, 2 hours, 3 hours, 4 hours, 8 hours, 12 hours, 16 hours or 24 hours. Lignin may also be contacted with a solid catalyst for a time ranging from about one day to about ten days or more. In some examples, lignin and a solid catalyst for lignin depolymerization may be contacted for a time period ranging from about 15 minutes to about one hour.

Degradation times and temperatures will vary based on the lignin source, solid catalyst used (e.g. an LDH), and the solvent used. Exemplary temperatures for lignin depolymerization by contacting lignin with a solid catalyst (e.g. an LDH) include temperatures of about 100° C., about 150° C., about 200° C., about 250° C., about 300° C., about 350° C. or about 400° C. For ethanol and MIBK solvents, suitable temperatures include at least about 150° C., about 185° C., about 270° C., or about 285° C. Suitable temperatures may range from about 100° C. to about 500° C., from about 200° C. to about 400° C., or from about 250° C. to about 350° C. In some examples, lignin may be contacted with a solid catalyst for lignin depolymerization at a temperature that ranges from about 100° C. to about 300° C.

Exemplary lignin-containing materials that may be depolymerized utilizing the solid catalysts describe herein (e.g. LDH) include lignocellulosic biomass such as bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure. Additional lignin-containing or lignin-like materials include those derived from microbial biomass feedstocks, such as algae, yeast or other fungi, molds, or bacteria.

Lignin may be degraded by contacting a lignocellulosic biomass directly with a solid catalyst (e.g. LDH). Alternatively, the lignocellulosic biomass may first be processed, purified or pretreated prior to being contacted with the catalyst. For example, the cellulose and hemicellulose components of lignocellulose may be at least partially removed prior to the step of contacting. Exemplary methods for at least partially purifying lignin from cellulose and hemicellulose include the Organosolv process (also known as Clean Fractionation or CF) or by preparing ball-milled lignin from biomass such as corn stover, as described in the Examples below. Any source of lignin, however, is suitable for use with the solid catalysts and methods described herein.

The resulting products after lignin depolymerization may also be fractionated, isolated, purified, and/or converted to additional products. For example, lignin depolymerization products (e.g. aromatic compounds) may be subsequently separated into different groups and/or compounds; e.g. by molecular weight, functional groups, etc. Lignin depolymerization products may also be converted to other chemical compounds via biological and/or chemical pathways.

Methods of fractionating, isolating or purifying lignin depolymerization products include a variety of chemical engineering unit operations. For example, the reaction mixture resulting from lignin depolymerization may be filtered to separate solid catalyst (e.g. LDH) from the lignin degradation products present in a liquid portion. Lignin depolymerization products may be further extracted from a solvent and/or purified using conventional methods. Exemplary methods for purification/isolation/separation of lignin depolymerization products include at least one of affinity chromatography, ion exchange chromatography, solvent extraction, filtration, centrifugation, electrophoresis, hydrophobic interaction chromatography, gel filtration chromatography, reverse phase chromatography, chromatofocusing, differential solubilization, preparative disc-gel electrophoresis, isoelectric focusing, HPLC, and/or or reversed-phase HPLC.

EXAMPLES

Materials

All solvents: acetone (HPLC grade, Fisher), ethanol (200 proof Pharmco-AAPER), methanol (lab grade, Fisher), diethyl ether (99.5%, Fisher), and methyl isobutyl ketone (reagent grade, Fisher) were used as received. 2-bromoacetophenone, phenol, potassium carbonate, potassium iodide, sodium borohydride, magnesium sulphate, nickel nitrate, and hydrotalcite were all purchased from Sigma-Aldrich and used as received.

Synthesis of Model Lignin Compound

For use as a model lignin compound in subsequent depolymerization assays, 2-phenoxy-1-phenethanol (PE) (200 in FIGS. 2A and 2B) was prepared according to published procedures as set forth below, and its purity was verified by comparison to published $^1$H and $^{13}$C NMR spectroscopic data. FIG. 2B illustrates a mechanism for the degradation of PE 200 to phenol 210 and acetophenone 220, whereby a β-O-4 bond 230 of the PE 200 is cleaved to produce phenol 210 and acetophenone 220. At least some of the solid catalysts described herein may be used to cleave β-O-4 bonds of other lignin molecules, reactants, and/or intermediates. Examples of lignin-related molecules, polymers, and model compounds, as well as lignin isolation processes, can be found in Zakzeski et al., Chem Rev, 2010, 110, 3552-3599.

Step 1: 2-Phenoxy-1-phenylethanone was synthesized in the following manner: A round bottom flask equipped with a reflux condenser was charged with 2-bromoacetophenone (1.1942 g, 60 mmol), phenol (7.0582 g, 75 mmol), $K_2CO_3$ (12.3000 g, 89 mmol), KI (catalytic) and acetone (250 mL). The resulting mixture was heated to reflux and allowed to react for 3 hours, after which it was filtered and concentrated. 2-Phenoxy-1-phenylethanone was crystallised from cold ethanol (250 mL) (85% yield).

Step 2: 2-Phenoxy-1-phenylethanone (1.1089 g, 5.2 mmol) was dissolved in 35 mL of methanol. Sodium borohydride (0.3534 g, 10.4 mmol) was added portion-wise generating a gentle evolution of gas, after which the reaction mixture was stirred at room temperature for 2 hours. The reaction was quenched with a saturated aqueous $NH_4Cl$ solution (30 mL). The resultant mixture was extracted with 20 mL diethyl ether three times. The combined organic extracts were dried with 50 mL saturated brine solution, dried over $MgSO_4$, and filtered. The filtrate was evaporated to dryness to afford an off-white solid of 2-phenoxy-1-phenylethanol (80% yield). The solid was dried overnight in a vacuum desiccator.

Synthesis and Characterization of Catalysts

The general procedure for the synthesis of the layered double hydroxide (LDH) materials is as follows, using MgAl-LDH as an example. Adjustments to the ratios of starting reagents can be made to alter the ratio of metal atoms in the products and are noted when applicable. An aqueous solution of metal-ion precursors with ratio Mg:Al of 3:1 was prepared by dissolving 30.87 g Mg$(NO_3)_2$.6H$_2$O (120 mmol) and 15.01 g Al$(NO_3)_3$.4H$_2$O (40 mmol) in 100 mL deionized water. A separate basic aqueous solution was prepared by dissolving 12.82 g NaOH (320 mmol) and 2.02 g $Na_2CO_3$ (20 mmol) in 100 mL deionized water. A 1 liter 3-neck flask was charged with 300 mL deionized water and a magnetic stir bar. Two dropping funnels were attached to the flask and charged with each solution. The solutions were rapidly added simultaneously to the 3-neck flask while stirring vigorously to form a solid white precipitate. After each solution had been added, the resulting suspension was heated to 80° C. and stirred vigorously for 18 hours. The solid material was centrifuged and rinsed with hot deionized water three times and dried in a vacuum oven to produce a white solid material.

The procedure for producing Ni-containing LDH material (NiAl-LDH) was the same as that for the MgAl-LDH material with the following exception: 34.89 g Ni$(NO_3)_2$.6H$_2$O (120 mmol) was used in place of Mg$(NO_3)_2$.6H$_2$O. Nickel-supported HTC was synthesized using wet impregnation, wherein Ni$(NO_3)_2$.6H$_2$O dissolved in ethanol was directly loaded onto commercial HTC. Three catalysts were initially synthesized at nickel loadings of 1.0, 5.0, and 11.0 wt % for screening purposes. Based on the desired weight loading, a solution of Ni$(NO_3)_2$.6H$_2$O in absolute ethanol was combined with the hydrotalcite support with constant stirring and this mixture was then left on a heating plate, at 25° C., to dry completely overnight. EA of 5 wt % Ni/HTC gave Al 10.46 wt. %, Mg 17.36 wt. %, and Ni 4.44 wt. %. Common post synthesis modifications of supported nickel catalysts often include calcination and reduction. Thus, two additional modified catalysts were synthesized and screened: 5 wt % Ni/HTC was calcined at 300° C. in air and a sample of 5 wt % Ni/HTC was reduced under 5% $H_2$ (He balance) at 250° C. for 2.5 hours. Unless specified, catalysts were used as synthesized without modification.

The general procedure for the synthesis of the Mg/Al porous metal oxide material (MgAl-PMO) is as follows. Isolated LDH material from the above preparations was calcined in a box furnace at 360° C. for 15 hours to remove any intercalating anions. After calcination, the material was rapidly transferred to a vacuum desiccator to cool under vacuum.

For characterization of catalyst materials, powder X-ray diffraction (PXRD) measurement was carried out using Cu Kα radiation in steps of 0.2° over the 2θ range of 10-80°. The resulting patterns were compared to known patterns in the ICDD database for hydrotalcite and poly-metal oxides containing Mg and Al.

Catalyst Activities

For tests of catalytic activity using model lignin compounds, a desired amount of catalyst, substrate, internal standard, and solvent were added to a 0.75 in swage union reactor. The reactor was sealed and placed in a fluidized sand bath and heated to the desired temperature (e.g., 110° C., 270° C. or 285° C.) for the desired time (e.g., one or two hours). At the end of the reaction, the reactor was carefully removed from the sand bath and placed in an ice-water bath for 5 minutes. Then, the reactor was opened and an aliquot of the liquid material was removed for analysis using GC/MS.

For tests of catalytic activity using biomass-derived lignin, reaction conditions were the same as those using model compounds, except a desired amount of isolated clean-fractionation lignin (prepared using an Organosolv biomass fractionation process, see Bozell et al., *Biomass and Bioenergy* 35:4197-4208 (2011)) was used. After the reaction, all materials were removed and each reactor was rinsed with a small amount (about 8 mL) of acetone to transfer any remaining solid residue. This material was acetylated using acetic anhydride and pyridine and analyzed using gel-permeation chromatography.

Figure 3A:
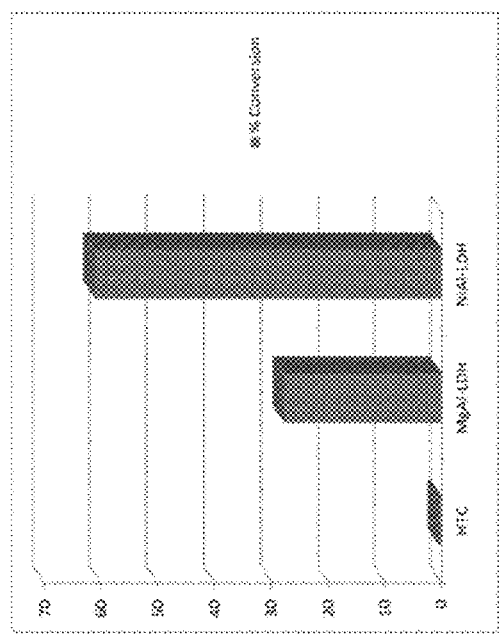
FIGS. 3A and 3B show graphs of the percentage conversion of lignin model compound PE in the presence of catalysts in a methyl isobutyl ketone (MIBK) solvent system (A) or in an ethanol solvent system (B), according to exemplary embodiments of the present invention. A comparison of commercial-grade hydrotalcite catalyst (HTC) with MgAl and NiAl layered double hydroxide catalysts is shown in each instance), according to exemplary embodiments of the present invention.

The results of the catalytic testing of the LDH materials in methyl isobutyl ketone (MIBK) are outlined in Table 1 and FIG. 3A. At 110° C. for 2 hours, no conversion of the model lignin compound was detected by GC/MS with any catalyst species. Commercial basic alumina and a 3:1 mixture of magnesium and aluminum hydroxide (Sigma Aldrich) were also tested as control experiments. Neither of these compounds showed any conversion under the same conditions.

At 285° C. ($T_{critical}$=300° C. for MIBK), the model lignin compound was converted to a variety of products in only 1 hour. Percentage conversion was measured using durene as an internal standard. By comparison, the commercial-grade hydrotalcite (HTC, Sigma Aldrich) showed less than 1% conversion, whereas MgAl-LDH and NiAl-LDH displayed much greater conversion (28 and 61%, respectively).

TABLE 1

| Catalyst | Temp, ° C. | Time, min | % Conversion |
| --- | --- | --- | --- |
| MgAl-LDH | 110 | 120 | 0 |
| Comm. HTC | 110 | 120 | 0 |
| MgAl-PMO | 110 | 120 | 0 |
| basic alumina | 110 | 120 | 0 |
| mixed hydroxides | 110 | 120 | 0 |
| MgAl-LDH | 285 | 60 | 28 |
| comm. HTC | 285 | 60 | <1 |
| NiAl-LDH | 285 | 60 | 61 |

Figure 3B:
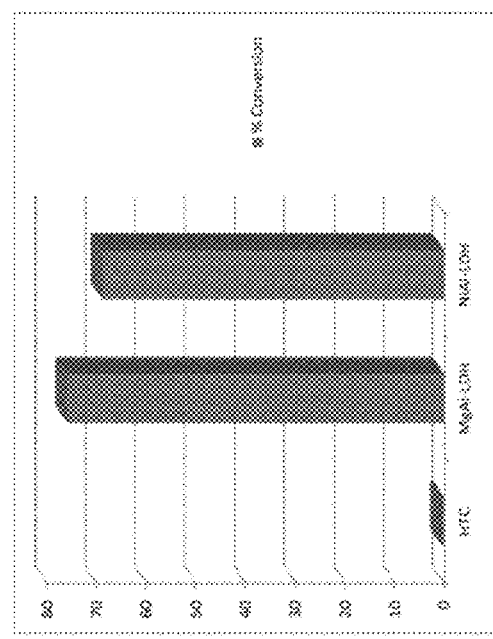

To test other relevant solvent systems, the same experiment was carried out using ethanol as a solvent rather than MIBK. The results of these experiments are outlined in Table 2 and FIG. 3B. At 285° C., which is above the critical temperature of ethanol, less than 5% conversion of the model lignin compound was detected in the absence of catalyst. In addition, conversion in the presence of commercial-grade hydrotalcite was less than 1%. However, conversion in the presence of MgAl-LDH and NiAl-LDH was substantial (76 and 69%, respectively).

TABLE 2

| Catalyst | Temp, ° C. | Time, min | % Conversion |
| --- | --- | --- | --- |
| none | 285 | 60 | <5 |
| MgAl-LDH | 285 | 60 | 76 |
| comm. HTC | 285 | 60 | <1 |
| NiAl-LDH | 285 | 60 | 69 |

Catalyst Screening Methods

Catalysts were screened via a heated batch reaction method. Catalysts were loaded into 3 mL stainless steel batch reactors and charged with 3 mL of stock solution giving PE or HH substrate to catalyst loading of 1:2. Experiments were run in triplicate. The reactors were tightly sealed and submerged in a heated temperature-controlled sand bath. Temperature was monitored with a thermal couple. After a designated time, the reactors were removed from the sand bath and the reaction was quenched immediately by inserting the reactors into an ice bath.

In the post reaction work up of products, the reactors were opened and the contents were centrifuged to collect the used catalyst. This catalyst was then washed with acetone, centrifuged, and left to dry for further analysis. The resulting solution was then brought up to a final volume of 10 mL with acetone. For the subsequent GC analysis, the products were diluted 10 times to bring final concentrations into calibrated range of about 0 mM to about 1 mM with a 1.0 mM durene internal standard. Samples were analyzed in an Agilent Technologies 7890A GC equipped with an FID detector employing an HP-5MS column (30 m×0.25 mm×film thickness 0.25 µm, Agilent Technologies). The temperature program was as follows: 45° C. hold for 3 minutes; ramp to 200° C. at 15° C./min hold for 6 minutes; total run time of 19.33 minutes. In all cases mass closures (based on conversion and production of phenol) were greater than 90%.

Catalyst Activities

Figure 2A:
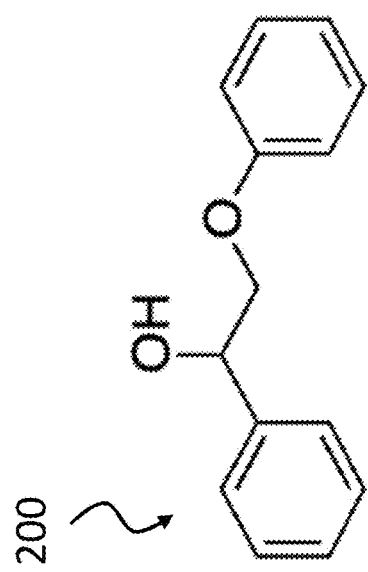
Figure 2B:
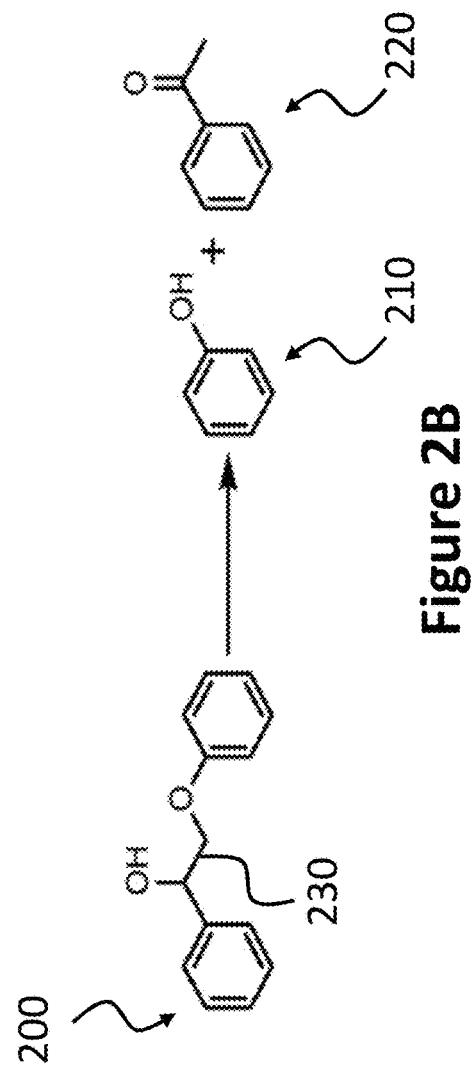
FIG. 2B shows the base-catalyzed α-O-4 bond cleavage in the model compound PE to produce phenol and acetophenone.

Catalytic activity was first screened on a lignin model compound 2-phenoxy-1-phenethanol 200 (PE), shown in FIG. 2A. PE is a representative lignin model compound containing a β-O-4 alkyl-aryl-ether bond, which is the most abundant inter-monomer bond in native lignin. A temperature of 270° C. was used for the initial catalyst screening. Methyl isobutyl ketone (MIBK) was used as the reaction solvent as it is a typical co-solvent used to fractionate biomass into its primary components in Organosolv processes. For each reaction, the catalyst of interest and a stock solution of PE dissolved in MIBK were loaded into a 3 mL stainless steel batch reactor at a loading of 2:1 wt:wt, catalyst:PE. Unless otherwise noted, catalysts were used as prepared without post synthesis modifications. The reactions were run at 270° C. for 1 hour in triplicate. The reaction mixture was washed from the reactor with a known amount of acetone and the catalyst was removed. In all cases, PE was converted to phenol and acetophenone (1-phenylethanone) by cleavage of the β-O-4 aryl-ether bond (see FIGS. 2A and 2B). The resulting solution was analyzed by gas chromatography for concentration of PE, phenol, and acetophenone.

Figure 4A:
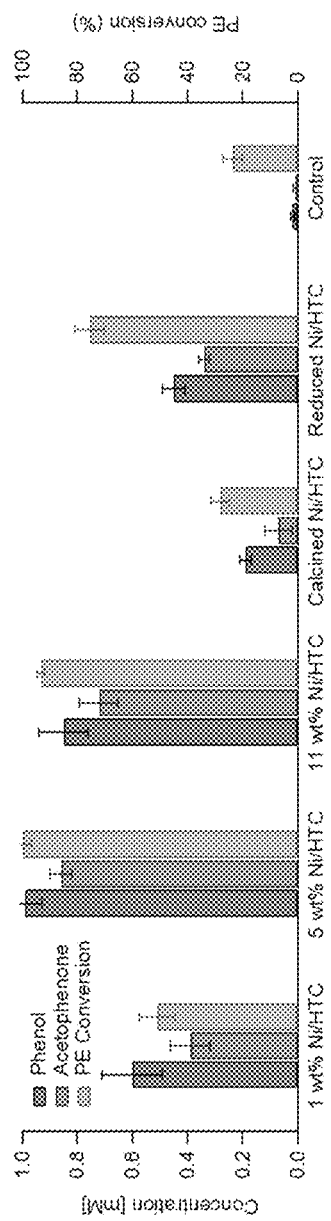
FIGS. 4A and 4B show results of catalyst screening with PE at 270° C. for 1 hour in MIBK (A) and results of secondary screening to ascertain the catalytic properties responsible for aryl-ether bond cleavage (B), according to exemplary embodiments of the present invention. The $Ni(NO_3)_2$, HTC, and $Ni/Al_2O_3$ reactions were conducted at 270° C. for 1 h in MIBK. The NaOH experiments were conducted in deionized $H_2O$. The original 5 wt % Ni/HTC results are shown for reference.

FIG. 4A details the results of the initial catalyst screening with 5 catalysts for activity on PE and a control run with PE and no catalyst. Under these conditions, the as-prepared, loaded Ni/HTC catalysts are the most active in PE conversion. Lowering the nickel loading from 11 to 5 wt % has little effect, and 1 wt % Ni/HTC still exhibits a conversion of about 50%. Little conversion was observed in the control reaction. Modification of the 5 wt % Ni/HTC catalyst via calcination or reduction lowers the activity to 28% conversion and 75% conversion, respectively. It is known that heating HTC can thermally remove the interstitial hydroxide anions (see FIG. 1A). As the hydroxide anions are hypothesized to be an active catalytic species and calcining may remove these species, it is perhaps not surprising that the calcined catalyst exhibits lower activity.

Additionally, LDH catalysts promote aldol condensation. A common result of the experiments illustrated in FIG. 4A as well as subsequent figures reporting conversion data for PE on HTC catalysts is the lower yield of acetophenone relative to phenol. GC/MS results suggest that MIBK undergoes a small amount of cross-condensation with acetophenone, as well as self-condensation reactions in the presence of HTC catalysts (data not shown), hence the acetophenone yield is lower. Mass closures of 90% and EDS (Table 3) indicate that little to no material is lost due to charring during reaction.

The results summarized in FIG. 4A demonstrate that 1, 5 and 11 wt % nickel-supported HTC are effective catalysts for cleavage of the β-O-4 bond. To ascertain the catalytic properties responsible for aryl-ether bond cleavage, a series of additional experiments were performed in which HTC alone (the support material containing interstitial hydroxide anions), $Ni(NO_3)_2$ (the loaded nickel species), and a 5 wt % $Ni/Al_2O_3$ catalyst (a standard supported nickel catalyst) were investigated as catalysts with PE. NaOH was also employed to determine if base-catalyzed cleavage produces the same reaction products. The $Ni(NO_3)_2$, HTC, and $Ni/Al_2O_3$ reactions were conducted at 270° C. for 1 hour in MIBK. The NaOH experiments were conducted in deionized $H_2O$. The original 5 wt % Ni/HTC results are shown for reference.

Figure 4B:
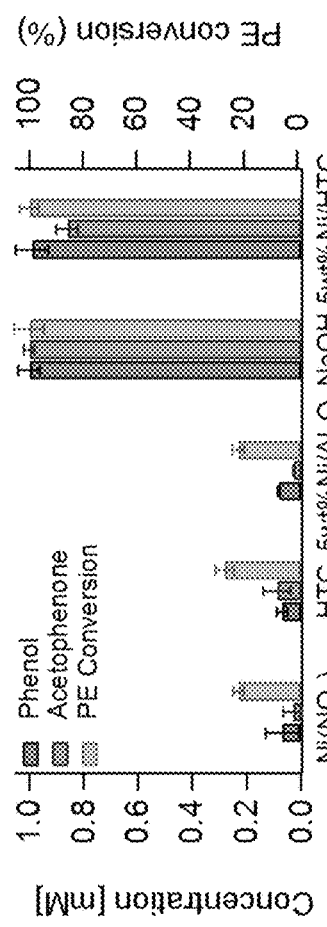

Results of these experiments are summarized in FIG. 4B. HTC alone and $Ni(NO_3)_2$ are not active catalysts, exhibiting only 28% and 23% conversion of PE respectively. The 5 wt % $Ni/Al_2O_3$ exhibits low, partial conversion of 23%. NaOH catalysis of PE in water produces the same product distribution as the HTC catalyzed-reaction, and the yield of acetophenone and phenol are equal here, further suggesting that HTC promotes aldol condensation of acetophenone and MIBK. Taken together, these results suggest that Ni/HTC catalytic activity is not a result of the individual species, but rather a synergistic effect between supported nickel and HTC, and that the mechanism follows one similar to base-catalyzed cleavage of PE.

Additionally, the effect of reaction temperature on PE conversion was studied using the 5 wt % Ni/HTC catalyst with a one hour reaction time (see FIG. 5A). PE conversion activity drops off at 150° C. with the majority of activity still remaining at 185° C. Activity was greatest at 270° C., showing over 90% PE conversion. Preliminary recycling studies (5 wt % Ni/HTC catalyst; 270° C.; one hour) show that the 5 wt % Ni/HTC catalyst maintains activity over 3 catalytic cycles (see FIG. 5B).

Biomass Fractionation Procedures

Clean Fractionation of corn stover was carried out as follows: Whole corn stover (10 g) in a single-phase mixture of MIBK/acetone/$H_2O$ (11/44/44 wt %, 100 mL) with sulfuric acid (0.1 M) was loaded into a Hastelloy pressure reactor. The reactor was sealed and heated in an electric heating block at 140° C. for 56 minutes. After the reaction, the reactor was cooled in ice water. Reaction mixture was filtrated and the residual solid was washed with the same solvent (200 mL) and deionized $H_2O$ (650 mL) to remove the soluble fraction completely. The combined black filtrate (MIBK/acetone/$H_2O$) was mixed in a separatory funnel, shaken, and allowed to stand for 1 hour to separate the aqueous and organic phases. The aqueous layer was extracted with MIBK (25 mL). MIBK layers were combined, washed with deionized $H_2O$, evaporated to remove volatiles, and dried in a vacuum oven at 35° C. for 4 days to obtain the lignin-enriched fraction.

Deacetylation, disk refining, and enzymatic hydrolysis (DDE) of corn stover were carried out as follows: whole corn stover was deacetylated in 0.1 M NaOH (8 wt % total solids) at 80° C. for 2 hours, then rinsed with 45° C. water until the pH was 8.5, and dried under flowing air. In some cases, an optional acid treatment step was incorporated after deacetylation to prevent microbial growth. If included, the acid was be $H_2SO_4$ at 0.8 wt % concentration (10 wt % with respect to the lignin), and the acid treatment was at room temperature for up to 2 hours. The resulting material, with or without acid preservation, was then disk refined to 1-5 mm particles. The refined material was then enzymatically hydrolyzed at 15 wt % solids and 50° C. for 72 hours in pH 5.1 $NH_4OH$-citrate buffer using Novozymes CTEC3 (cellulase) and HTEC3 (xylanase) enzymes at 60 mg protein/g cellulose and 40 mg protein/g cellulose, respectively. These processes increased the lignin content from about 15.2 wt % in the starting biomass to about 35.5 wt % in the isolated DDE lignin.

Dilute acid pretreatment (DAP) of corn stover was carried out as follows: whole corn stover was treated at 8 wt % total solids in 0.8 wt % $H_2SO_4$ at 160° C. for 10 minutes, then neutralized to pH 5.1 and enzymatically hydrolyzed under the same conditions as the DDE lignin. These processes increased the lignin content from about 15 wt % in the starting material to about 61.3 wt % in the isolated DAP lignin.

Gel Permeation Chromatography (GPC) Analysis

After the catalytic degradation of CF-lignin (20 mg), the reaction mixture and wash solvent (10 mL of acetone) was filtrated through a 0.2 μm nylon membrane syringe filter. The filtrate was concentrated to approximately 2 mL using a gentle stream of nitrogen gas. The degradation mixture was acetylated for purposes of enabling the GPC method in a mixture of pyridine (0.5 mL) and acetic anhydride (0.5 mL) at 35° C. for 24 hours with stirring. The reaction of acetylation was terminated by addition of methanol (0.2 mL) to neutralize the acetic anhydride. The acetylation solvents were then evaporated from the samples at 40° C. under a stream of $N_2$. The samples were further dried in a vacuum oven at 40° C. overnight. The dried acetylated degradation products were dissolved in tetrahydrofuran (THF, Baker HPLC grade) to a final concentration of 2 mg/mL. The dissolved samples were filtered (0.45 μm nylon membrane syringe filters) before GPC analysis. The acetylated samples appeared to be completely soluble in THF. GPC analysis was performed using an Agilent HPLC with 3 GPC columns (Polymer Laboratories, 300×7.5 mm) packed with polystyrene-divinyl benzene copolymer gel (10 μm beads) having nominal pore diameters of 104, 103, and 102 Å. The eluent was THF and the flow rate was 1.0 mL/min. An injection volume of 25 μL was used. The HPLC was attached to a diode array detector measuring absorbance at 260 nm (band width 40 nm). Retention time was converted into molecular weight by applying a calibration curve established using polystyrene standards.

Degradation of Biomass-Derived Lignin

To determine if the 5 wt % Ni/HTC catalyst can degrade biomass-derived lignin, it was tested with lignin from an Organosolv process, Clean Fractionation (CF), at 270° C. for 1 hour in MIBK, and also tested with corn stover derived, ball-milled lignin (CS-BML) at 270° C. for 1 hour in water. Apparent molecular weights (MW) obtained by gel permeation chromatography (GPC) are provided in FIG. 6A (CF lignin) and FIG. 6B (CS-BML). A control reaction was also carried out in which the CF lignin was heated to 270° C. in MIBK (or CS-BML heated to 270° C. in water) to quantify uncatalysed degradation.

The original CF lignin shows a large MW range from 300-10,000 Da. Upon heating in MIBK ("Control" in FIG. 6A), the CF lignin exhibits lower MW due to thermal decomposition (from about 200 to about 2,000 Da). However the MW of the CF lignin run with the 5 wt % Ni/HTC catalyst in MIBK was substantially reduced, with a significant portion of material present as monomeric species (the GPC measurements for lignin are only semi-quantitative, and should primarily be interpreted as relative trends). The "CF Lignin" curve shows the molecular weight distribution of the original lignin from an Organosolv process. The "Control" and "5 wt % Ni/HTC" curves show the molecular weight distributions after reaction (270° C., 1 hour) of thermal and catalytic degradations, respectively, of the CF lignin.

FIG. 6B shows that the CS-BML heated in water ("Control") also undergoes partial thermal depolymerization, and the catalyzed reaction ("5 wt % Ni/HTC") produces a significant amount of small molecular-weight species. The "CS-BML" curve shows the molecular weight distribution of the original lignin after ball milling. The "Control" and "5 wt % Ni/HTC" curves show the molecular weight distributions after reaction (270° C., 1 hour) of thermal and catalytic degradations, respectively, of the ball-milled lignin.

X-Ray Diffraction

X-Ray Diffraction (XRD) was conducted on powdered samples using a Rigaku Ultima IV diffractometer with a Cu $K\alpha$ radiation source (40 kV and 44 mA). Scans were collected from 10-80° $2\theta$ with a step size of 0.01° using a dTex detector. Diffraction data were processed using Rigaku PDXL software, and peaks were matched against the International Centre for Diffraction Data (ICDD) database PDF 2009.

Interaction of the loaded nickel species with HTC and the fate of nickel in the 5 wt % Ni/HTC catalysts during reaction were studied before and after one PE conversion (2:1 catalyst loading, 270° C., 1 hour) using XRD. A change in the color of the catalyst was noted after reaction. The freshly prepared Ni/HTC catalyst is light green, and after reaction the catalyst is black. The XRD pattern of the catalyst (See FIG. 7A) indicates that nickel in the bulk material is present as mainly $Ni(OH)_2$ rather than the loaded $Ni(NO_3)_2$ species. The prominent peak at 20° is from $Ni(OH)_2$, which arises from nickel interacting with the HTC. The XRD pattern of the used catalyst shows that under the reaction conditions (270° C.), features from a dehydrated HTC structure arise, as seen in the shift of the (003) peak at 11.4° $2\theta$ to a higher angle and broadening of the (009) peak at 35° $2\theta$. The peaks arising from $Ni(OH)_2$ species ($2\theta=19.8°$, 37.8°, and 43.5°) seen in the fresh catalyst shift for the used catalyst with the prominent peaks characterized as a mixed valence nickel oxide ($2\theta=21.1°$, 36.9°, and 43.0°). This may indicate that the $Ni(OH)_2$ species (which is green) is converted to the mixed valence nickel oxide during reaction (which in its oxygen rich, non-stoichiometric structure is black). As shown in FIG. 7B, the recycling study indicates that the mixed valence nickel oxide species is still as active in PE conversion.

X-Ray Photoelectron Spectroscopy

X-Ray Photoelectron Spectroscopy (XPS) analysis was performed using a Physical Electronics PE5600 XPS system. Samples were pressed into indium foil. Spectra were collected using a monochromatic Al $K\alpha$ X-ray source operated at 350 W, hemispherical analyzer, and multichannel detector. A low-energy (~1 eV) electron flood gun was used for charge neutralization. Survey spectra were collected using an analyzer pass energy and step size of 187.85 eV and 0.8 eV/step, respectively. High-resolution spectra were collected using an analyzer pass energy of 23.50 eV and a step size of 0.1 eV/step. The quantification was performed using the default relative sensitivity factor (RSF) values supplied by the XPS manufacturer. Data analysis was performed using CasaXPS software. A linear background was applied to C1s, O1s and N1s spectra and Shirley background was used for Ni 2p and Mg 1s spectra. High-resolution spectra were charge referenced by setting the C 1s hydrocarbon peak to 284.8 eV.

To gain further insight into the fate of nickel, XPS analysis was conducted on the same freshly prepared 5 wt % Ni/HTC catalyst as well as the 5 wt % Ni/HTC catalyst that had been used once for PE conversion (e.g. used catalyst as in FIG. 7B). XPS analysis of the fresh catalyst indicates that nickel is present as $Ni(OH)_2$ and $Ni(NO_3)_2$ as demonstrated by the asymmetry of the peak envelope centered at 856.8 eV. As XPS is quite sensitive to surface species, it is not surprising that $Ni(NO_3)_2$, which is not observed in XRD analysis, is present in the spectra. This species combined with $Ni(OH)_2$ (confirmed in both XRD as well as XPS) is responsible for the light green color of the freshly synthesized catalyst. The presence of $Ni(OH)_2$ in the XPS spectrum confirms that there is indeed an interaction when nickel is loaded onto the HTC support that will immediately convert some of the $Ni(NO_3)_2$ to $Ni(OH)_2$. $Ni(OH)_2$ is tightly bound to the support and is insoluble in both water as well as MIBK, as experimentally confirmed via hot water washes in which no nickel species were lost as indicated from SEM/EDS analysis (Table 3). After reaction, the peak formerly centered at 856.8 eV has sharpened and shifted to a slightly lower energy of 855.5 eV, indicating that both $Ni(NO_3)_2$ (and likely $Ni(OH)_2$ as indicated by XRD) have converted to a mixed valence nickel oxide, which is responsible for the visually observed dark color in the used catalyst. There are no changes in binding energy of 852-853 eV that would indicate appearance of Ni0, further indicating that changes in catalyst are due to conversion to nickel oxide species rather than reduction. This result is corroborated by the lower activity of the reduced catalyst shown in FIG. 4A relative to the high activity maintained over several runs by the mixed valence nickel oxide catalyst, as shown in FIG. 7B.

Microscopy and Energy Dispersive X-Ray Spectroscopy

Scanning Electron Microscopy (SEM) was performed using a FEI Quanta 400 FEG instrument. Samples were mounted on aluminum stubs with conductive carbon tape adhesive and sputter-coated with 7 nm of iridium prior to imaging. Images were obtained at an accelerating voltage of 30 keV.

Energy Dispersive X-Ray Spectroscopy (EDS) was performed in the aforementioned SEM instrument equipped with an EDAX X-ray detector using the same sample preparation methods used for SEM imaging. Elemental composition was obtained from at least 5 EDS spectra collected at each experimental condition; spectra were quantified using an atomic number (ZAF) correction. EDS mapping was performed in Quant mode based on net intensity using dwell time of 200 ms per pixel.

For Transmission Electron Microscopy (TEM), catalyst particles were suspended in ethanol and drop-cast onto carbon coated, 200 mesh copper grids (SPI Supplies, West Chester, Pa.). Grids were allowed to air dry and images were captured with a four mega-pixel Gatan UltraScan 1000 camera (Gatan, Pleasanton, Calif.) on a FEI Tecnai G2 20 Twin 200 kV LaB6 TEM (FEI, Hilsboro, Oreg.).

SEM imaging provides insight as to why Ni/HTC is an active catalyst. HTC particles are on the order of ten of microns; however, the particles are agglomerates of nanoscale subunits, giving rise to a high surface area, macroporous network with pore diameters ranging from about 0.1 to 1 µm (see FIGS. 8A-D). These pores are large relative to other catalysts, such as microporous zeolites, which are routinely used for conversion of petroleum-based and biomass-derived small molecular weight species. The larger pore sizes displayed by the HTC catalysts used in this study appear better suited to facilitate heterogeneous interaction with solubilized lignin polymers. Interestingly, no discernible changes to the catalyst microstructure were observed following chemical reaction (see FIGS. 8A-D).

SEM imaging of fresh 5 wt % Ni/HTC shows that loading the nickel did not disrupt the highly porous substructure of the HTC support (see FIG. 9A). The nanostructure of the catalysts was further investigated by TEM (see FIGS. 9B-D). These images illustrate that the individual nanoscale subunits of the larger catalyst particles are largely devoid of meso and micro pores, and further supports that the macroporosity of the bulk catalyst particles is formed by the agglomeration of these constituents. An atomic layered structure of the catalyst may be observed in the high magnification image provided in FIG. 9D.

Elemental mapping of the catalyst particles revealed a largely uniform distribution of nickel throughout the catalyst at the microscale (see FIG. 9$h$), with no evidence of phasing or localized clusters of nickel present at this scale. Interestingly, no loss of nickel from the catalyst support was detected after reaction (see Table 3), indicating that there was no metal leaching during the reaction. These results support the observation of a robust incorporation of nickel into the catalyst support that is resistant to leaching and structural degradation at the reaction conditions employed in this study.

TABLE 3

EDS Elemental Analysis of LDH Catalysts - Elemental Composition (Wt %)

| Sample | Carbon | Oxygen | Magnesium | Aluminum | Nickel |
|---|---|---|---|---|---|
| Pre-reaction | 17.0 ± 4.2 | 53.3 ± 2.1 | 17.8 ± 1.9 | 8.3 ± 1.0 | 3.0 ± 0.4 |
| Post-reaction | 17.9 ± 5.0 | 45.1 ± 1.2 | 19.0 ± 3.4 | 11.9 ± 2.1 | 6.0 ± 0.8 |
| Catalyst Wash | 19.5 ± 7.4 | 52.7 ± 2.8 | 18.5 ± 3.7 | 8.8 ± 2.3 | 3.2 ± 0.6 |

Preparation of Ball-Milled Lignin

Ball-milled lignin (BML) was prepared from extractives-free corn stover according to the Björkman method. Corn stover was extracted with water and ethanol for 48 hours, respectively, using a soxhlet extractor. Air-dried extractives-free corn stover was ground in toluene at 4° C. for 2 weeks, in ceramic jars (0.3 L volume) using ceramic balls under a nitrogen atmosphere. Ball-milled corn stover (1096 g) was extracted with 1.5 L of 96% dioxane (v/v) for 2 days with vigorously stirring. The suspension was filtered and solid residue was extracted with the same solvent for additional 2 days. Combined filtrate was evaporated at 40° C. under reduced pressure to obtain crude BML (31.3 g). The crude BML was dissolved in 90% acetic acid and precipitated into water. The precipitate was collected by centrifugation and then washed with water 3 times until acetic acid was removed. Freeze dried precipitate was dissolved into 85 mL of 1,2-dichloroethane/ethanol (2:1, v/v) and precipitating into diethyl ether (800 mL). The precipitate was recovered by centrifugation (18000 rpm, 10 minutes) and then washed with ether 2 times to obtain corn stover BML (14.4 g, 1.32 wt %). The lignin and carbohydrate contents in the BML were 84.4 and 7.51 wt %, respectively.

Catalyst Preparation

Figure 10:
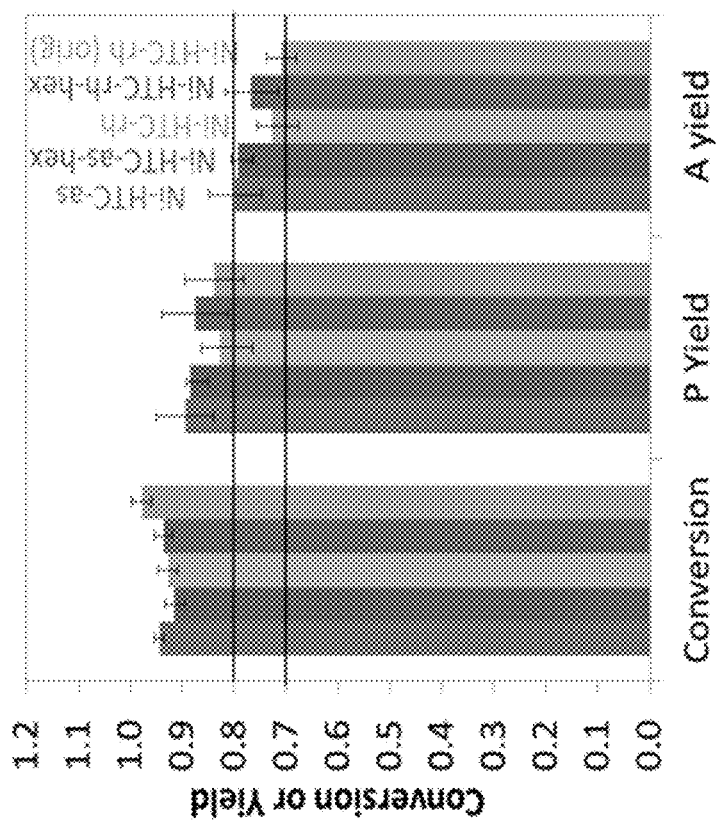
FIG. 10 shows experimental data comparing the activity of some embodiments of the present invention, nickel treated LDH catalysts prepared by different methods, according to exemplary embodiments of the present invention.

The following general procedure was used for the various additional examples that follow below. Catalysts were prepared from as-synthesized commercially available hydrotalcite (HTC-as which designates "as-synthesized commercially available hydrotalcite"). Calcination may generate a higher surface-area MgO-type mixed oxide with some Mg atoms substituted by Al (HTC-ca which designates "calcined hydrotalcite"). Rehydration may restore the hydrotalcite structure, but with OH– anions instead of $CO_3^{2-}$, potentially yielding a more strongly basic catalyst (HTC-rh which designates "calcined-and-rehydrated hydrotalcite"). A hexane washing step, was included in some cases to potentially remove residual manufacturing oils (see FIG. 10). Typically, for catalysts prepared from HTC-as, the hexane-washing step was included, but for catalysts prepared from HTC-rh, it was not. The residual oils were removed in the calcination step regardless of hexane washing. Metal loading was typically accomplished by depositing a metal precursor salt as an ethanolic solution, to give a loading of 5 wt % metal. A typical reaction employed a 3-mL stainless steel high-pressure batch reactor, with 40 mg of catalyst and 3 mL of 33 mM PE in the desired solvent (13.3 mg catalyst/mL solution). This procedure gave a metal/PE ratio of 0.1 g/g. Reaction pressure was the autogeneous pressure generated by the equilibrium vapor pressure of the solvent and any gaseous products formed during reaction.

Preliminary Screening of Catalysts

A preliminary screening of fourteen catalysts synthesized from different metal precursor salts was carried out. All of the catalysts prepared from nitrate precursors performed well in the conversion of PE to phenol and acetophenone (see FIG. 2). All of the catalysts from chloride precursors did not perform well, and were no more active than blank hydrotalcite (see FIG. 11).

Solvent Screening

Figure 12:
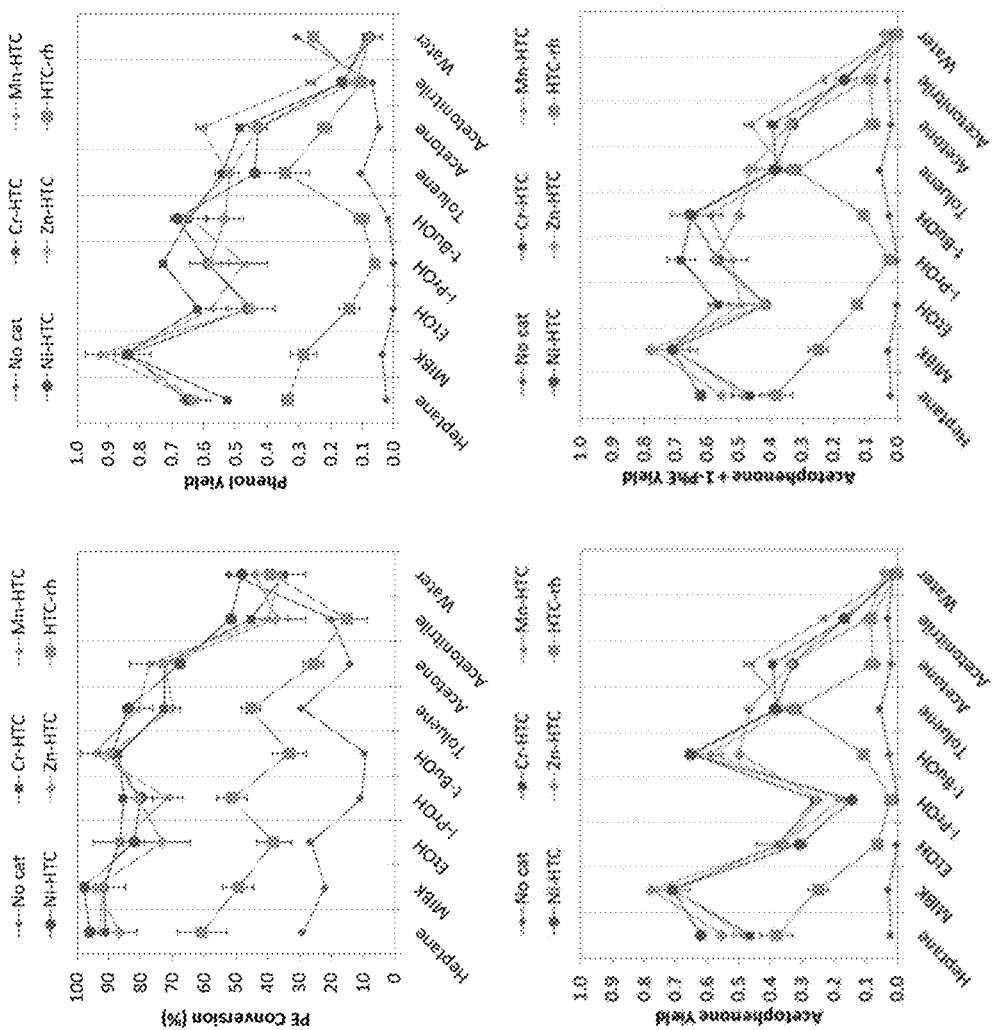
FIG. 12 shows experimental data comparing the performance of various LDH catalysts prepared with and/or incorporating different solvents and metals, according to exemplary embodiments of the present invention.

A number of solvents give high PE conversions, but MIBK appears to be the most suitable solvent in terms of acetophenone and phenol yields (see FIG. 12). Solvent parameters related to solvent molecular size, such as molar volume, Van der Waals volume, and to a lesser extent, molecular weight, show a reasonable correlation with solvent performance. Thus, large molecular-size solvents appear to perform well, and alcohol solvents provide the relative best performance.

Figure 13:
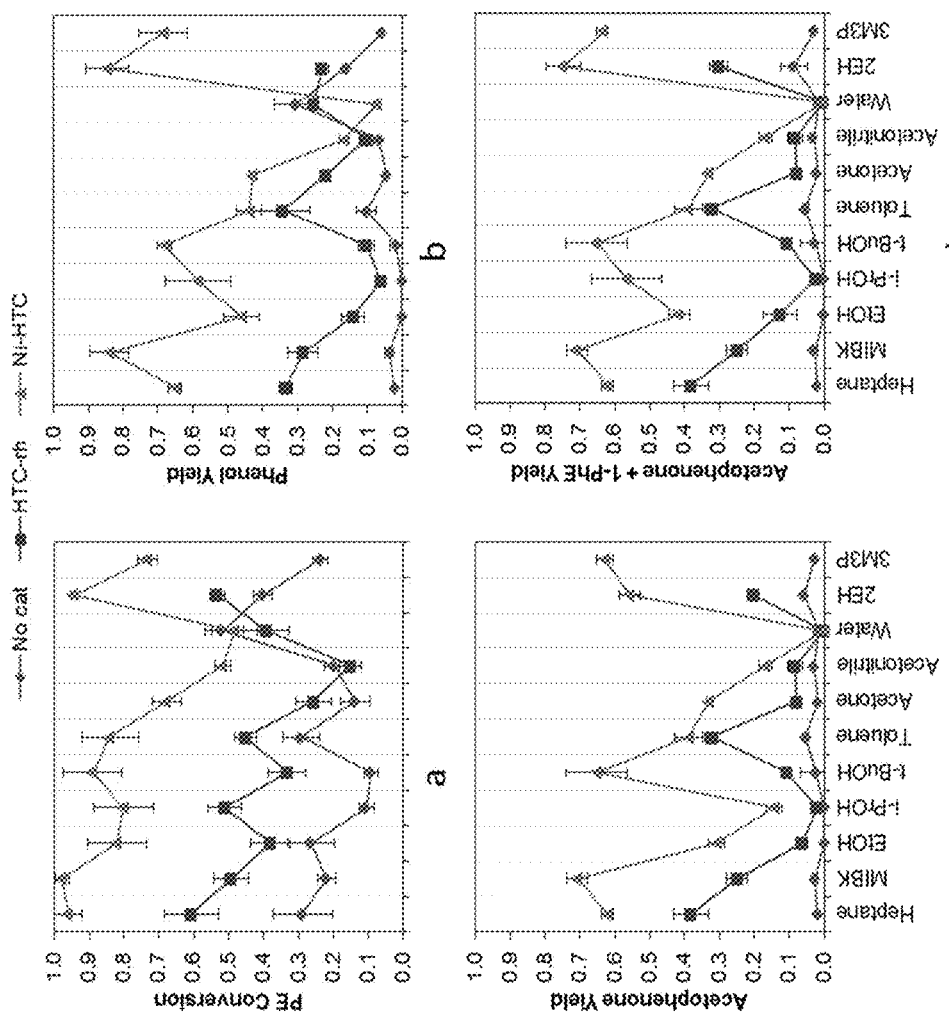
FIG. 13 shows catalyst performance in a solvent screening study in terms of (a) PE conversion (b) phenol yield, (c) acetophenone yield, and (d) combined yield of acetophenone and 1-phenylethanol, showing transfer hydrogenation from EtOH, i-PrOH, and 2EH. MIBK: methylisobutyl ketone. EtOH: ethanol. i-PrOH: isopropanol. t-BuOH: tert-butanol. 2EH: 2-ethylhexanol. 3M3P: 3-methyl-3-pentanol.

To test additional solvents, blank HTC-rh and Ni-HTC-rh were used as catalysts. Generally, the Ni-HTC-rh gave much higher activity than blank HTC-rh or the control reaction. Conversion of PE across the solvents investigated is shown in FIG. 13 along with yields of phenol, acetophenone, and combined yield of acetophenone and 1-phenylethanol. In ethanol and isopropanol solvents, significant 1-phenylethanol is produced, likely by transfer hydrogenation from the solvent to acetophenone. Similar transfer hydrogenation has been observed over Ni—Al LDH-derived materials.

There is significant variation in both PE conversion and monomer yields among solvents, with heptane, MIBK, tert-butanol (t-BuOH), 2-ethylhexanol (2EH), and 3-methyl-3-pentanol (3M3P) showing the highest performance. The poor performance of some of the other solvents may result from low PE solubility, which may limit the interaction of PE and the catalyst (water, toluene), or possible adsorption onto and poisoning of active basic sites in the catalyst (acetonitrile).

Catalyst Characterization

Figure 14:
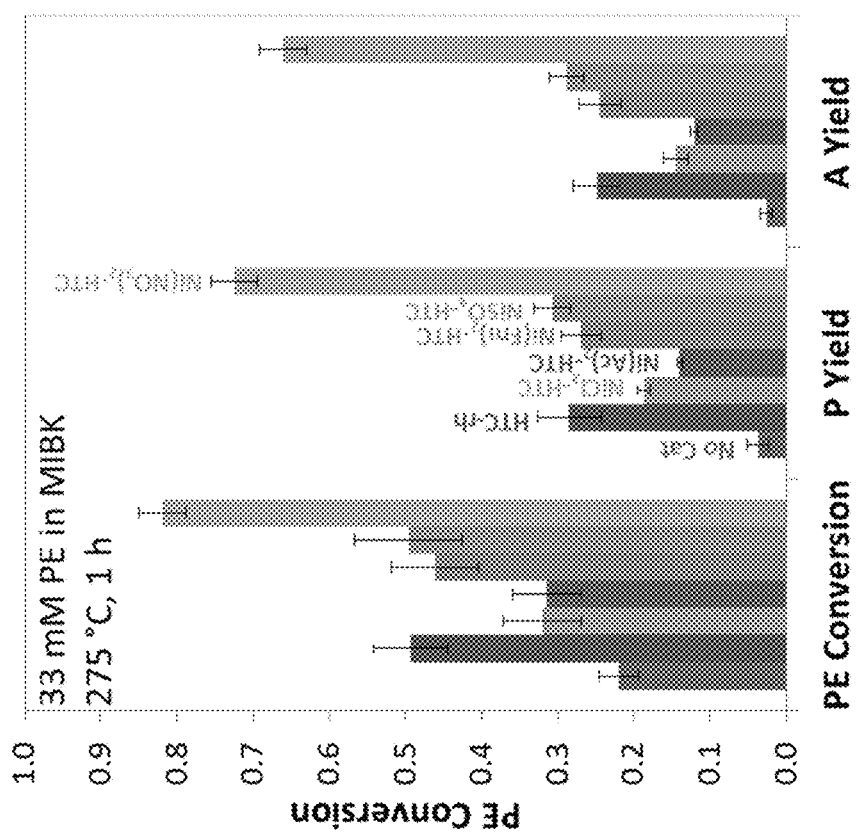
FIG. 14 shows experimental data for LDH catalysts contacted with various metal salts, wherein the anion ($A^{n-}$) is varied, according to exemplary embodiments of the present invention.

Initial screening studies suggest that catalysts prepared from nitrate precursor salts may perform better than catalysts prepared from chloride salts. Therefore, Ni-HTC catalysts were synthesized from other precursor salts to further explore this effect, and the results are presented herein. Catalysts prepared from sulfate, formate, and acetate, as well as chloride salts preform no better than blank hydrotalcite, and in some cases appear to have even lower activity than the blank (see FIG. 14).

XRD shows that the catalysts prepared from nitrate precursors yielded additional peaks not present in the parent hydrotalcite samples. These peaks, at $2\Theta=10°, 20°, 38°$, and $43°$, were originally hypothesized to arise from a separate $M(OH)_2$ phase, but on closer inspection were determined to originate from a partial intercalation of $NO_3^-$ anions into the hydrotalcite structure. These peaks represent the 003, 006, 015, and 018 reflections, shifted to a lower $2\Theta$ due to increased interlayer spacing. While the planar $CO_3^{2-}$ anions are positioned parallel to the planes of the HTC structure, the $NO_3^-$ anions, although also planar, are tilted toward the z-axis, resulting in a taller gallery between brucite layers. This partial intercalation was also present in catalysts prepared from all of the other metal nitrate precursor salts (see FIG. 15).

Attempts were made to decouple the effect of the metal from the effect of the nitrate by preparing a metal-free HTC catalyst by ion-exchanging HTC-as with $NO^{3-}$ from $NaNO_3$. This catalyst also exhibited the characteristic peaks in the XRD traces. Additionally, we attempted to synthesize a Ni-HTC-rh catalyst by rehydrating calcined HTC in a solution of 1 M $Ni(NO_3)_2$ instead of deionized water. This catalyst turned a uniform green color, suggesting Ni incorporation, but lacked the XRD peaks from $NO_3^-$ intercalation. Additionally, this catalyst was less crystalline than HTC rehydrated by the original procedure. The lack of $NO_3^-$-incorporation may be due to the strong preference of the HTC structure for the smaller $OH^-$ anion. It is hypothesized, and without wishing to be bound by theory, that this method may be more effective when rehydrating in a wet ethanol solution of $Ni(NO_3)_2$ instead of aqueous, although it may also be possible to synthesize HTC with $NO_3^-$ ions directly.

The ion-exchanged catalyst (HTC-as($NO_3$)) also showed a high activity in conversion of PE to phenol and acetophenone in MIBK, while the HTC rehydrated in 1 M aqueous $Ni(NO_3)_2$ was inactive, confirming that the $NO_3^-$ is the key active phase.

Catalyst Washing

Figure 15:
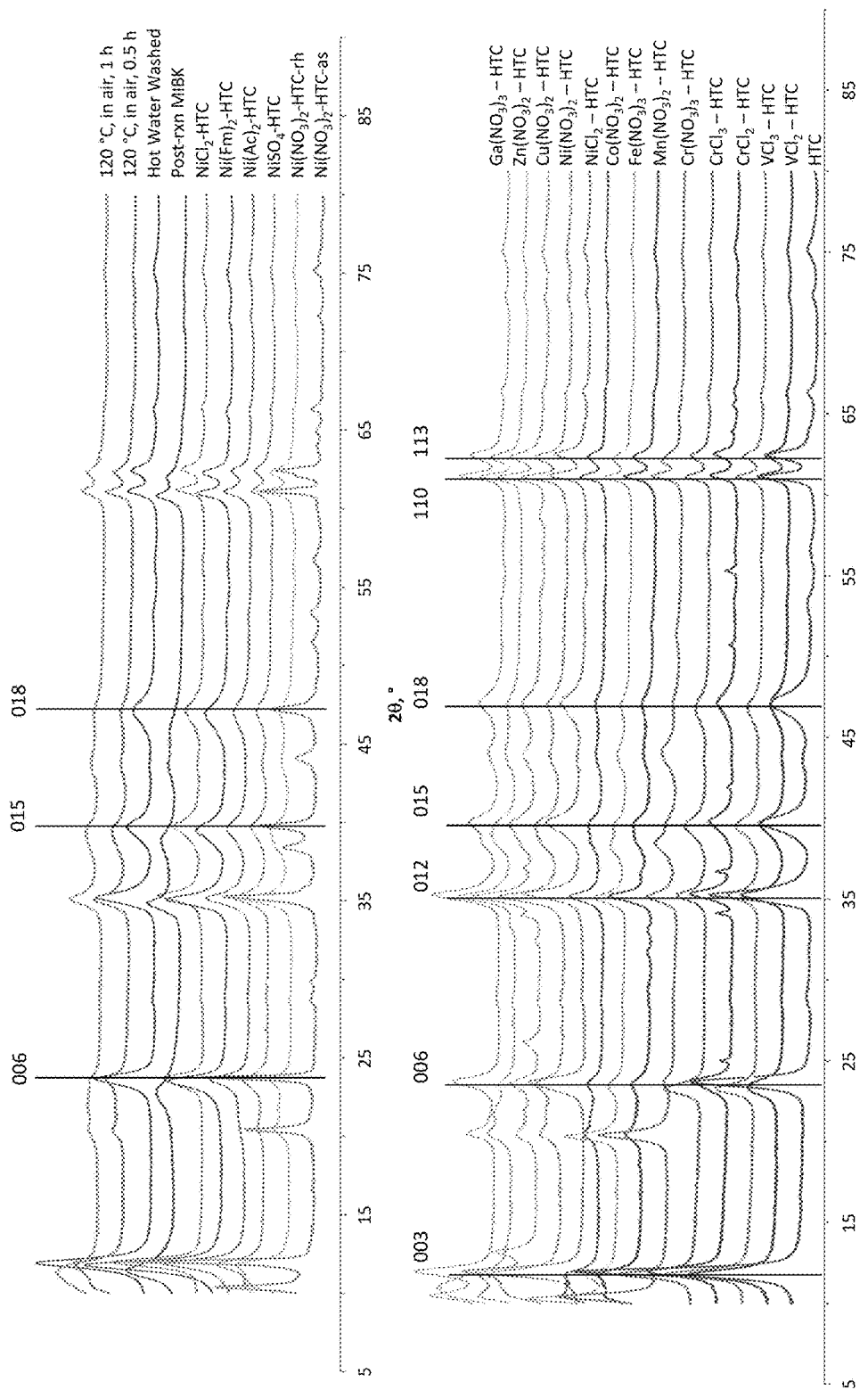
FIG. 15 illustrates XRD data characterizing some of the embodiments of the present invention, LDH catalysts for lignin depolymerization.

Illustrated in FIG. 15 is XRD characterization of HTC catalysts prepared by deposition of $Ni(NO_3)_2$, but subjected to different post-synthesis treatments. These treatments show that the intercalated $NO_3^-$ is relatively labile, as washing with hot water completely removes the extra peaks, and baking at 120° C. for 1 h or reaction with PE in MIBK decreases their relative intensity.

The extraction of $NO_3^-$ by washing with hot water was confirmed by quantifying $NO_3^-$ anions in the wash water with a nitrate ion-selective electrode. The levels of $NO_3^-$ washed off the catalyst are 35-40% of the total deposited $NO_3^-$ for Ni-HTC-as and 25-30% of the total for Ni-HTC-rh. These levels match well with the levels of Ni detected in the washes by atomic absorption spectroscopy, which are about 35% and 26% of the deposited Ni for Ni-HTC-as and Ni-HTC-rh, respectively (Table 4 below). These levels suggest that some of the deposited Ni may be converted to $Ni(OH)_2$ (i.e., incorporated into the HTC structure), while some remains in the $Ni(NO_3)_2$ form. The amount of Ni washed off the catalysts prepared from different precursors ranges from 2.5% for the formate to 22.5% for the chloride, suggesting that the precursor salt may determine how strongly the metal interacts with the hydrotalcite.

TABLE 4

| Catalyst | ppm Ni | % Ni washed |
| --- | --- | --- |
| HTC-rh | <0.1 | — |
| $Ni(NO_3)_2$-HTC-rh | 187 | 26.1% |
| $Ni(NO_3)_2$-HTC-as | 253 | 35.4% |
| $Ni(Ac)_2$-HTC-rh | 136 | 19.0% |
| $Ni(Fm)_2$-HTC-rh | 18 | 2.5% |
| $NiCl_2$-HTC-rh | 161 | 22.5% |
| $NiSO_4$-HTC-rh | 72 | 10.0% |

Quantification of Catalyst Physicochemical Properties and Other Data

Because heterogeneous catalysis is often a function of surface area, we characterized the catalysts by $N_2$ physisorption to understand how the surface area changes across different catalyst treatments, as shown in Table 5. The surface areas show that the hexane washing step has minimal effect relative to all other treatments, with the exception of the calcined HTC, for which the hexane-washed sample shows lower surface area. However, loading Ni and calcining HTC increase the surface area significantly, while rehydrating the calcined sample decreases the surface area, but not to the level of HTC-as, consistent with the XRD patterns discussed above.

TABLE 5

| Catalyst | BET Surface Area (m²/g) |
| --- | --- |
| HTC-as | 8.4 |
| HTC-as-hex | 10.1 |
| HTC-ca | 137.5 |
| HTC-ca-hex | 103.4 |
| HTC-rh | 28.0 |
| HTC-rh-hex | 32.7 |
| Ni-HTC-as | 19.6 |
| Ni-HTC-as-hex | 16.5 |
| Ni-HTC-rh | 50.4 |
| Ni-HTC-rh-hex | 44.8 |

Figure 16:
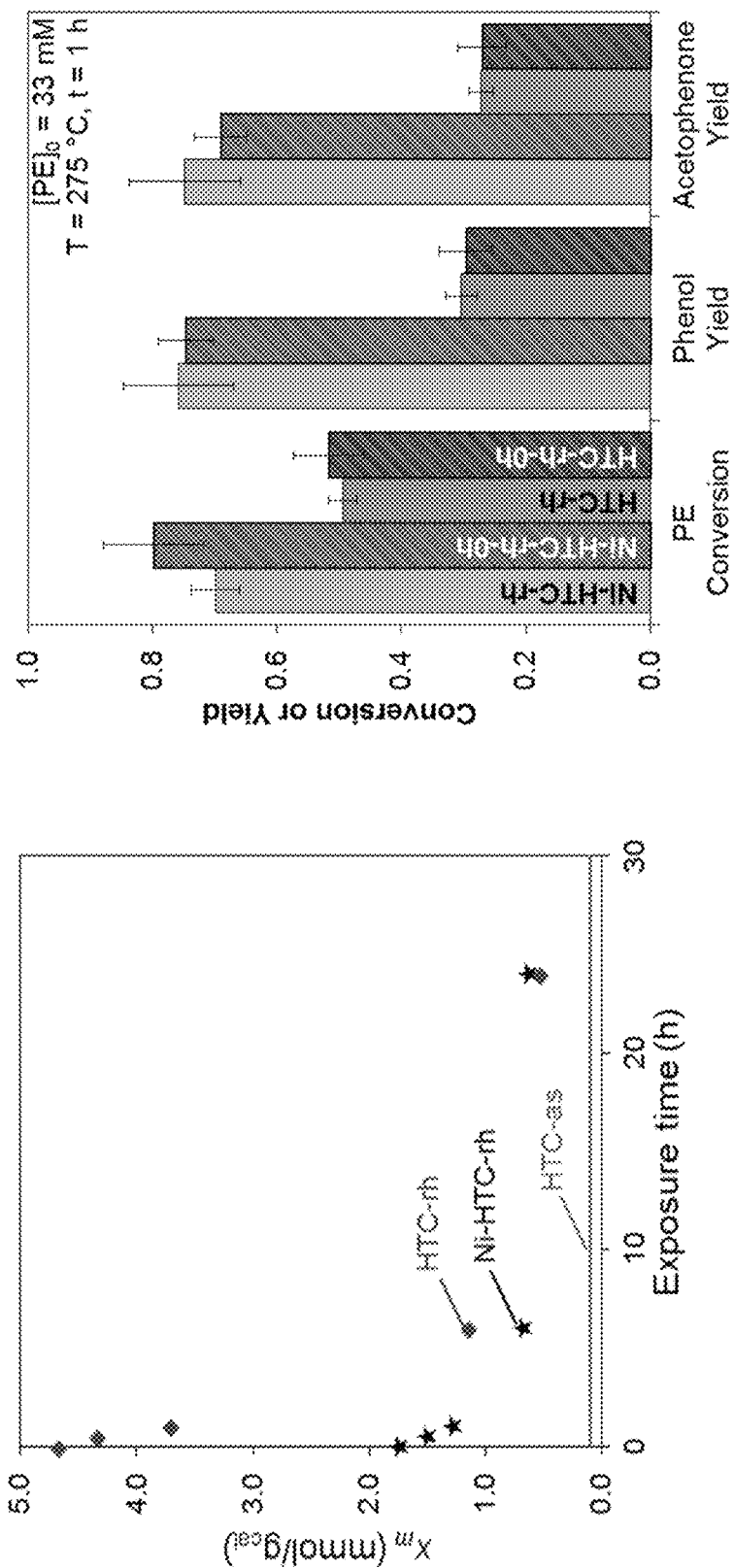
FIG. 16 illustrates basic site concentrations for LDH catalysts for lignin depolymerization and corresponding conversion data, according to exemplary embodiments of the present invention.

Because hydrotalcites are most commonly known for their basic characteristics, the basic sites were quantified by benzoic acid titration. Three sets of catalysts were examined in these titrations to explore different treatments on catalyst basicity. First, rehydrated hydrotalcites may undergo deactivation when exposed to air presumably due to poisoning by atmospheric $CO_2$. $CO_2$ may adsorb on basic $OH^-$ sites, potentially converting them to the much more weakly basic $CO_3^{2-}$. Thus, rehydrated hydrotalcites were prepared with minimal air exposure, and then exposed to atmosphere for a controlled amount of time. The concentration of basic sites on the catalysts decreases with increasing exposure to the atmosphere, as shown in FIG. 16 (left). However, the activity of the catalyst is the same at 24 hour exposure as at 0 hour exposure, despite different concentrations of basic sites by at least a factor of three, as shown in FIG. 16 (right). HTC-as, shown for reference, exhibits a much lower concentration of basic sites than HTC-rh, which may be partially due to lower accessibility of $CO_3^{2-}$ anions as a result of lower surface area.

Second, the basic sites of Ni-HTC-rh catalysts prepared from different precursors were titrated. The basic site concentrations ranged from 0.3-0.7 mmol/gcat, but again the catalyst activity did not appear to correlate with basic site concentration.

Figure 11:
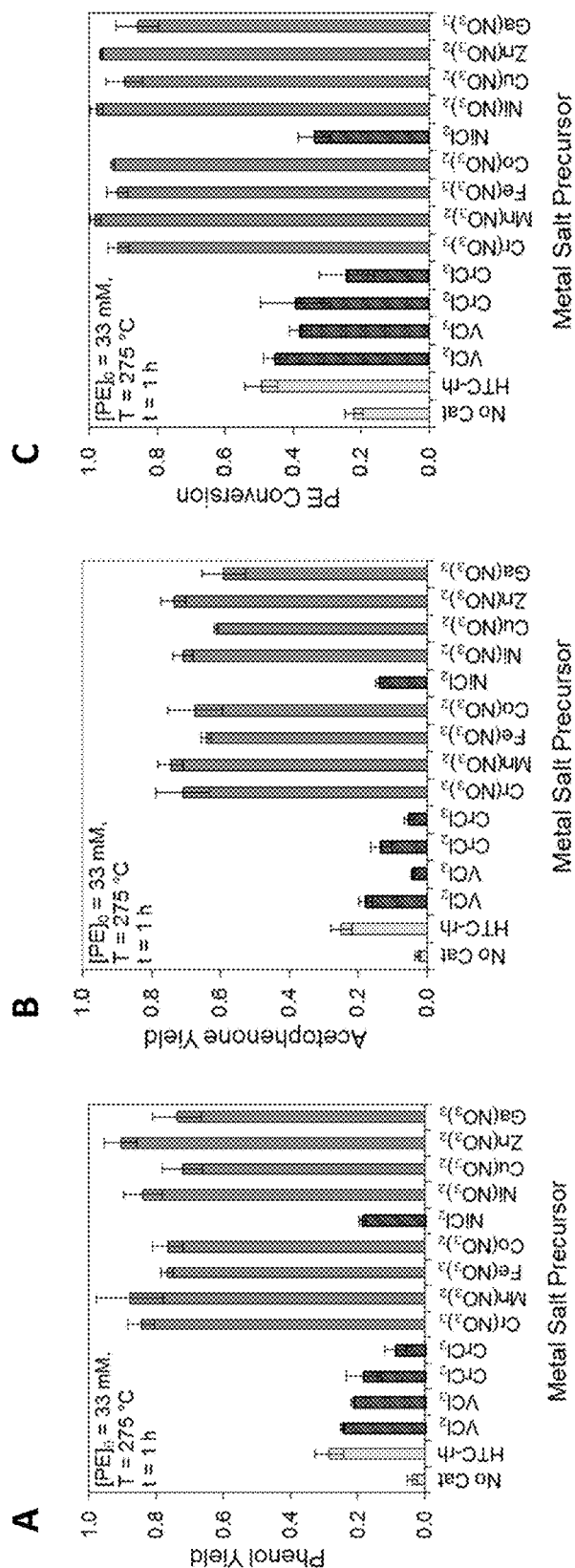
FIG. 11 shows (A) phenol yield, (B) acetophenone yield and (C) PE conversion experimental data comparing the performance of various metal treated LDH catalysts, according to exemplary embodiments of the present invention.
Figure 17:
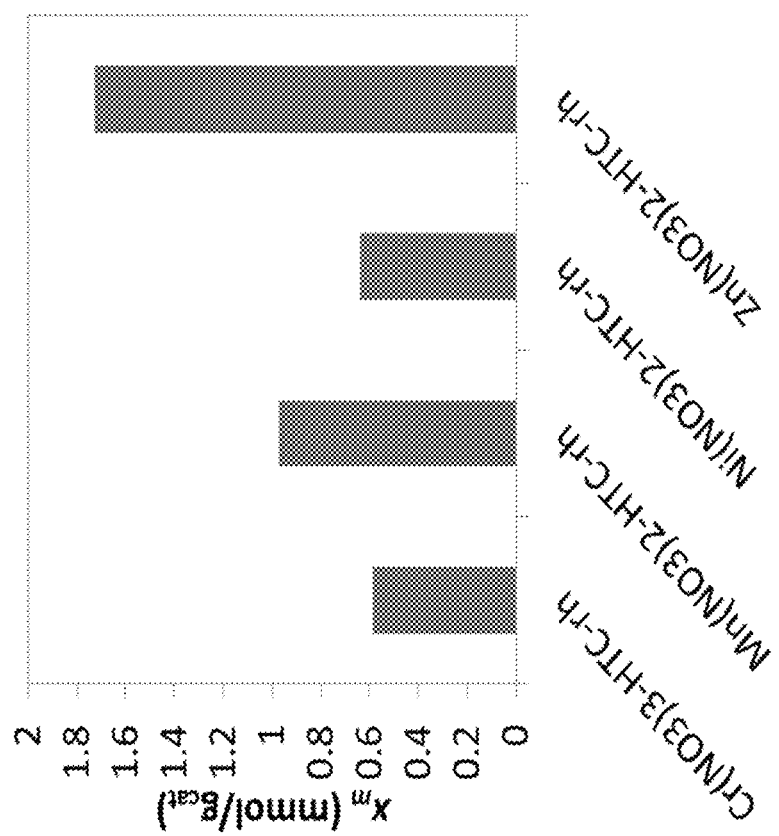
FIG. 17 compares the catalytic activity of different metal nitrates, according to exemplary embodiments of the present invention.

Finally, HTC-rh catalysts produced from different metal nitrate precursors were titrated. As shown in FIG. 17, there appears to be a difference between the different metals, although the activity of these catalysts is similar, as shown in FIG. 11. The difference may be due to differences in $NO_3^-$ intercalation into the catalyst structure; more $NO_3^-$ intercalated may correspond to more $OH^-$ displaced, and a lower basic site concentration measured. Thus, although all of the metals prepared from $NO_3^-$ salts performed comparably in the initial screening, it may be advantageous in terms of catalyst lifetime to select catalysts that show a lower basic site concentration, as it may indicate a higher degree of incorporation of the active $NO_3^-$ anions. That is, as $OH^-$ anions are replaced by $NO_3^-$ anions, the number of basic sites titrated by benzoic acid may decrease because of fewer $OH^-$ sites, but catalyst activity/lifetime may likely increase because of more $NO_3^-$ sites.

Without wishing to be bound by theory, the role of the nitrate in lignin depolymerization may include the following three possible mechanisms:

1. Nitrate may increase the accessibility of basic sites by increasing the d-spacing between brucite layers in the HTC structure.
2. Nitrate may act as an oxidant, possibly producing PE ketone as an intermediate, which has a weaker β-O-4 linkage.
3. Nitrate may act as a radical source, initiating a radical reaction that leads to β-O-4 bond scission.

Figure 18:
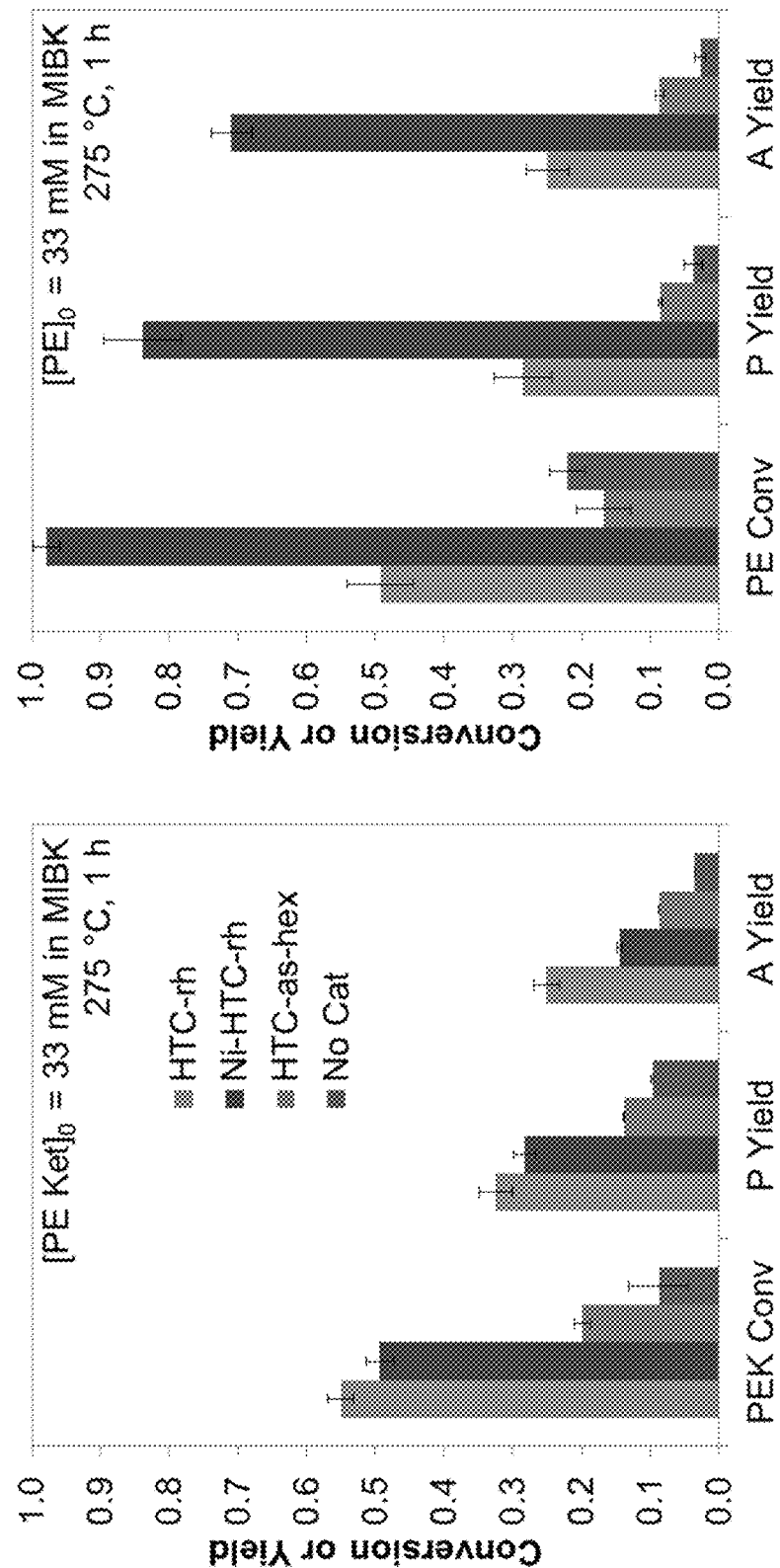
FIG. 18 compares the catalyst activity toward PE ketone and PE, according to exemplary embodiments of the present invention.

In the first scenario, increased conversion of PE ketone, which has similar molecular dimensions, should also be observed. However, as shown in FIG. 18, the ketone shows similar conversion as the alcohol over the blank catalyst, but not the nitrate-loaded catalyst. Thus, the role of the nitrate does not appear to be due to an increase in the accessibility of the basic sites.

Concerning nitrate as an oxidant, such a mechanism may be the oxidation of PE to PE ketone, which may then be converted to phenol and acetophenone. The comparison of PE ketone and PE seems to be consistent with this result: once the alcohol has been oxidized to the ketone, no further benefit of the nitrate can be observed. However, the ketone is never observed in high concentrations. Such a scenario is plausible if the ketone is a rapidly converted intermediate, but in that case, the conversion of PE ketone when used as a starting material would be expected to be significantly higher than the PE alcohol, which does not appear to be the case. Thus, the ketone does not appear to be a rapidly consumed intermediate.

To gain insight into whether or not a nitrate may act as an oxidant, HTC-as was ion-exchanged with $CrO_4^{2-}$ (from $K_2CrO_4$), another common oxidizing agent. Additionally, we added an external oxidant to the reaction solution as $NaNO_3$ and $Ce(SO_4)_2$. As shown in FIG. 18, the $CrO_4^{2-}$ ion-exchanged HTC-as is inactive. Addition of $NaNO_3$ to the reaction solution does not appear to affect PE conversion, but appears to increase the yields of phenol and acetophenone; $Ce(SO_4)_2$ in solution appears to increase both PE conversion and phenol yield, but apparently does not increase nor decrease acetophenone yield. The variation between oxidizing additives suggests that oxidation chemistry may play a role in catalyst activity, however the relative oxidizing potentials of $NO_3^-$, $HCrO_4^-$, and $Ce^{4+}$ (taking $HCrO_4^-$ as representative of $Cr^{6+}$) are +0.96V, +1.20 V, and +1.44 V, respectively, showing that $NO_3^-$ is, in fact, the weakest oxidant of the group. Thus, the activity of the nitrate is apparently not solely redox driven.

Evaluation of Salt Precursor on Lignin Depolymerization Activity

Figure 19:
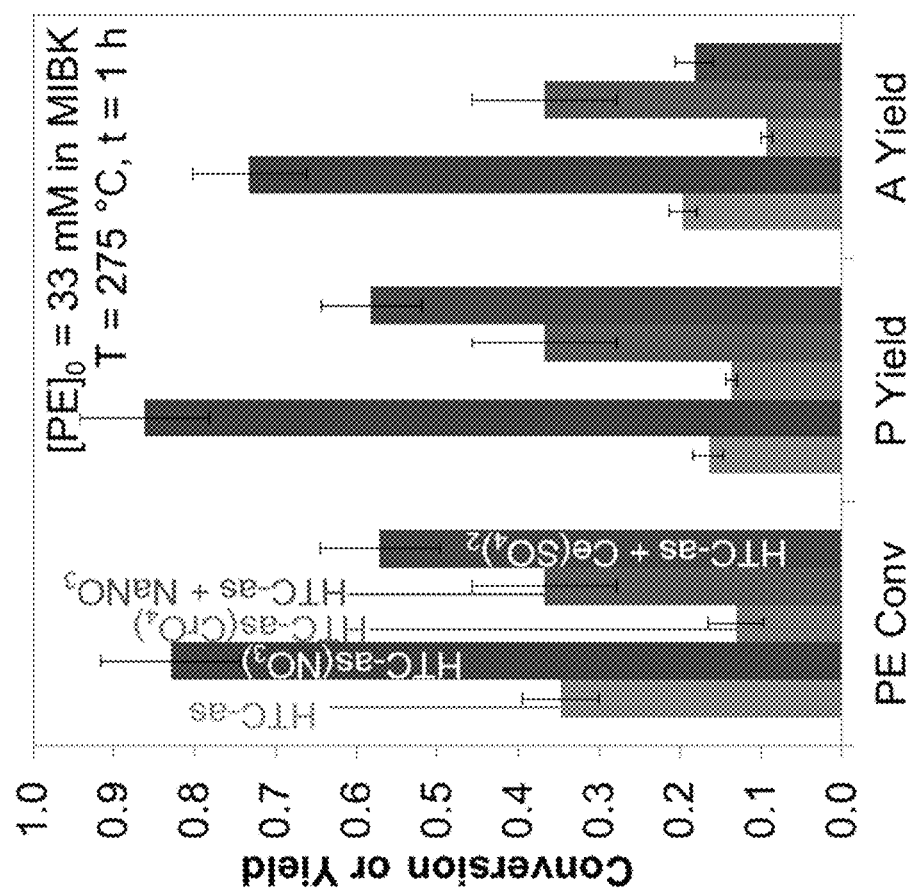
FIG. 19 shows the performance of various LDH catalysts exchanged with differing oxidizing anions, according to exemplary embodiments of the present invention.
Figure 20:
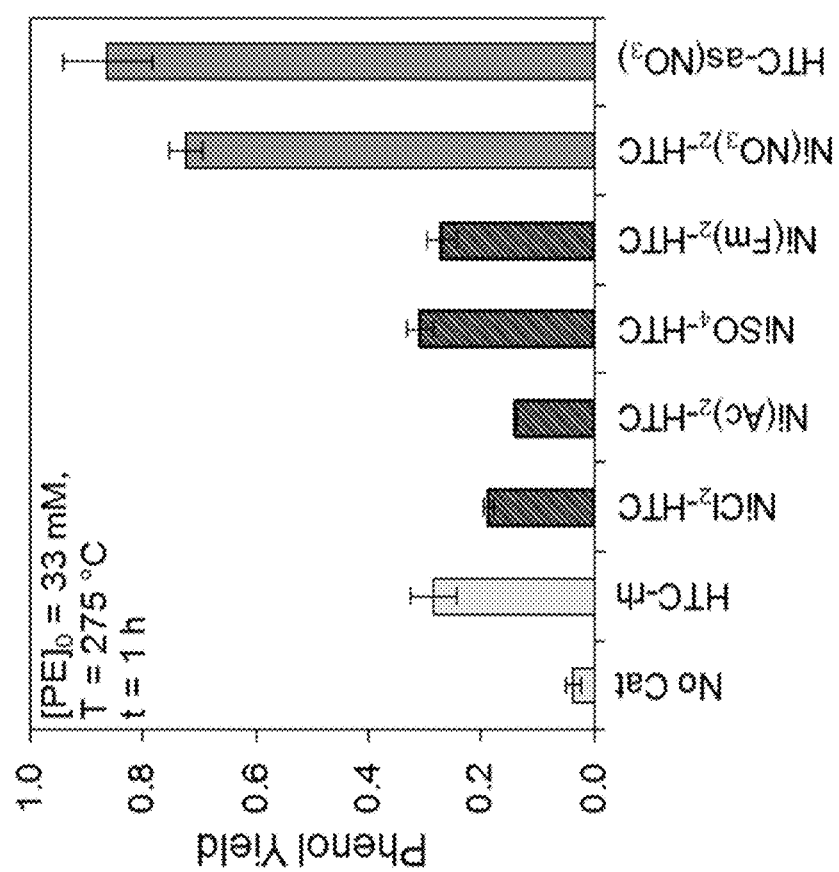
FIG. 20 illustrates the activity of Ni-HTC-rh catalysts prepared from different precursor salts, according to exemplary embodiments of the present invention.

Evaluation of HTC catalysts prepared from different salt precursors resulted in the data presented in FIGS. 19 and 20. A base case catalyst was prepared by calcining commercial HTC (HTC-as) at 450° C. for 16 hours to generate the mixed oxide form (HTC-ca). The calcined form was rehydrated by stirring in deionized water for 1.5 hours and sonicating in the same water for 5 minutes to generate the meixnerite form (HTC-rh). A solution of $Ni(NO_3)_2 \cdot 6H_2O$ in ethanol was added to give a nominal Ni loading of 5 wt %; the slurry was stirred for 5 min and dried overnight to give Ni-HTC-rh. In this preparation, all calcining, drying, and storage of prepared catalyst were done in open atmosphere with no effort to exclude $CO_2$. For comparison, uncalcined HTC was washed with hexanes to remove residual carbonaceous material from the manufacturing process and loaded with 5 wt % Ni; this catalyst is labeled Ni-HTC-as. Other metal catalysts were prepared as for Ni-HTC-rh, substituting the appropriate precursor for $Ni(NO_3)_2 \cdot 6H_2O$. Because anhydrous $VCl_2$, $VCl_3$, and $CrCl_2$ were not soluble in ethanol, these were prepared from aqueous solution.

A second set of catalysts was prepared by ion exchange methods. Briefly, a known amount of HTC-as was immersed in a solution of acid (HCl or $HNO_3$) and sodium salt (NaCl or $NaNO_3$). The acid concentration was such that the molar ratio $H+:CO_3^{2-}=2$, and the salt concentration was generally >2 M. To obtain an XRD-pure Cl-−form catalyst, two steps with concentrated NaCl were required; the second step did not incorporate acid. From the Cl-−exchanged catalyst, an additional ion exchange was performed with $NaNO_3$ to generate a fully nitrate-exchanged catalyst.

Two series of catalysts were prepared by varying the time exposed to atmosphere. For the first set, commercial HTC was calcined in air at 450° C. for 16 h to generate the mixed oxide form, and removed from the furnace hot (~250° C.). This HTC-ca was placed in a round-bottom flask and immediately flushed with $N_2$. Deionized water was added to the flask, and the slurry was stirred for 1 h under flowing $N_2$, sealed with a rubber septum, and sonicated for 5 min. This catalyst was filtered by vacuum filtration in a $N_2$ atmosphere and dried overnight under flowing $N_2$. When dry, this catalyst was transferred to an open-top vessel exposed to air. One-gram samples were taken periodically from this HTC-rh, placed in glass vials, purged with $N_2$, and sealed with a rubber septum and Parafilm to study the adsorption of $CO_2$ onto the rehydrated form as a function of atmospheric exposure time. These samples are labeled HTC-rh-xh, where x is the number of hours exposed to atmosphere.

For the second set, HTC-rh was prepared without exposure to $CO_2$ as described above for the first set, and a solution of $Ni(NO_3)_2 \cdot 6H_2O$ in ethanol was added to give a nominal Ni loading of 5 wt %. The slurry was stirred for 5 min and dried overnight under flowing $N_2$ to give the Ni-HTC. When dry, this catalyst was transferred to an open-top vessel exposed to air. One-gram samples were taken from this Ni-HTC, placed in glass vials, purged with $N_2$, and sealed with a rubber septum and Parafilm to study the adsorption of $CO_2$ onto the nickel-loaded, rehydrated form as a function of atmospheric exposure time. These samples are labeled Ni-HTC-xh, where x is the number of hours exposed to atmosphere.

To understand the role of the anion, Ni-HTC-rh catalysts were prepared with different Ni precursor salts. $NiCl_2.6H_2O$ and $NiSO_4.6H_2O$ were prepared from ethanolic solutions as for the $Ni(NO_3)_2.6H_2O$ precursor. Due to the low solubility of $Ni(HCOO)_2.2H_2O$ and $Ni(CH_3COO)_2.4H_2O$ in ethanol, the $Ni(HCOO)_2.2H_2O$ catalyst ($NiFm_2$-HTC-rh) was prepared from an aqueous precursor solution and the $Ni(CH_3COO)_2.4H_2O$ catalyst ($NiAc_2$-HTC-rh) was prepared from a methanolic solution. PE conversion, phenol yield and acetophenone yield show similar trends, as shown in FIG. 11. These results demonstrate that, regardless of metal, all catalysts prepared from nitrate precursor salts exhibit high activity, whereas those prepared from chloride salts are no more active, or in some instances less active, than the blank HTC-rh.

Figure 21:
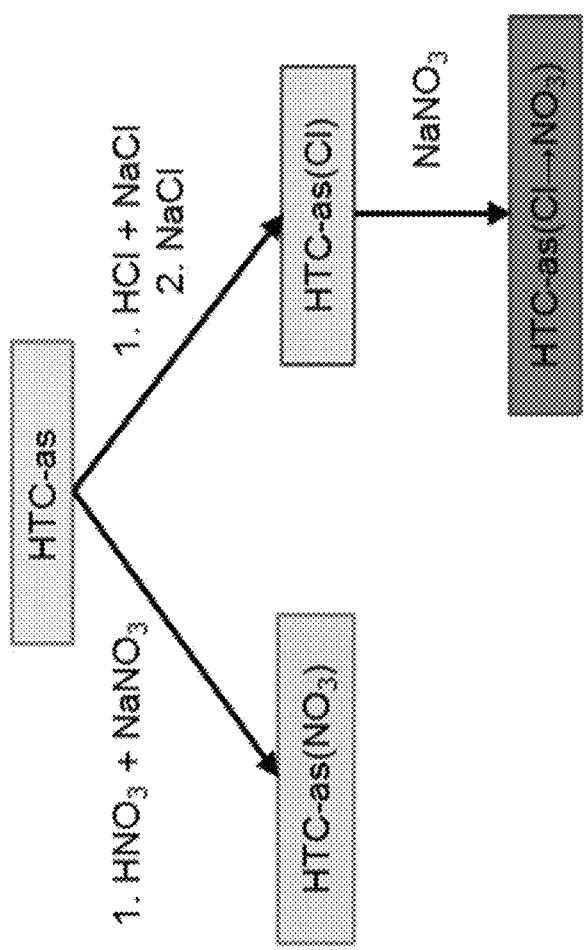
FIG. 21 shows a method for preparing catalysts to obtain ion-exchanged HTC catalysts, according to exemplary embodiments of the present invention.

To evaluate the impact that the salt precursor has on the overall catalyst activity, we prepared a series of Ni-HTC-rh catalysts from acetate, formate, and sulfate precursors. As summarized in FIG. 20, the other precursor salts also produce catalysts that are no more active, or less active, than the blank HTC-rh. To determine if the metal plays a significant role, we prepared a metal-free, ion-exchanged HTC-as, in which the $CO_3^{2-}$ anions were replaced by $OH^-$ and $NO_3^-$ anions (HTC-as($NO_3$), preparation described in FIG. 21). The activity of this catalyst is as high as the Ni$(NO_3)_2$-loaded catalyst, as shown in FIG. 20. This result demonstrates that a nitrate precursor enhances catalyst activity beyond blank HTC.

Although a transition metal-free catalyst would be advantageous in terms of cost and toxicity, the deposition of $NO_3^-$ from an alcohol solution is a convenient method of catalyst preparation that generates minimal waste compared to, e.g., ion exchange procedures. However, some embodiments of the present invention may also employ ion-exchange methods for depositing a nitrate or potentially other anion onto a solid support such as an HTC.

PE conversion, phenol (P) yield, and acetophenone (A) yields from nitrite ($NO_2^-$) ion-exchanged HTC-as, and nitrate ($NO_3^-$) deposited onto HTC-as from $Mg(NO_3)_2$ and $Al(NO_3)_3$ precursors were compared to other HTC catalysts. As shown in Table 6, nitrite-exchanged HTC did not enhance catalytic activity beyond that exhibited for the blank solid support.

TABLE 6

| Catalyst | PE Conversion | P Yield | A Yield |
|---|---|---|---|
| No Cat | 0.22 | 0.04 | 0.03 |
| HTC-as | 0.35 | 0.16 | 0.20 |
| HTC-as(NO$_2$) | 0.27 | 0.03 | 0.04 |
| HTC-as(NO$_3$) | 0.83 | 0.86 | 0.73 |
| Mg(NO$_3$)$_2$-HTC-as | 0.80 | 0.56 | 0.58 |
| Al(NO$_3$)$_3$-HTC-as | 0.64 | 0.41 | 0.40 |
| Ni(NO$_3$)$_2$-HTC-as | 0.91 | 0.88 | 0.79 |

Recycle and Regeneration

A recycle and regeneration study was performed evaluating the ability to replenish nitrate on an HTC structure. For recycle studies, larger Parr batch reactors (Parr Series 5000 Multiple Reactor System) were used to more efficiently generate sufficient catalyst for characterization after each reaction cycle. These reactions were scaled up by a factor of ten from the 3 mL reactors, and stirred at 400 rpm. After each reaction cycle, the catalyst from each reactor was combined to produce a pool of catalyst samples from which samples were withdrawn for characterization; the remaining catalyst was distributed to reactors for the next reaction cycle. For catalyst regeneration, the spent catalyst was calcined for 16 hours at 450° C., then rehydrated and reloaded with an ethanolic solution of $Ni(NO_3)_2$ by the same procedure used to generate fresh Ni-HTC-rh.

Figure 22:
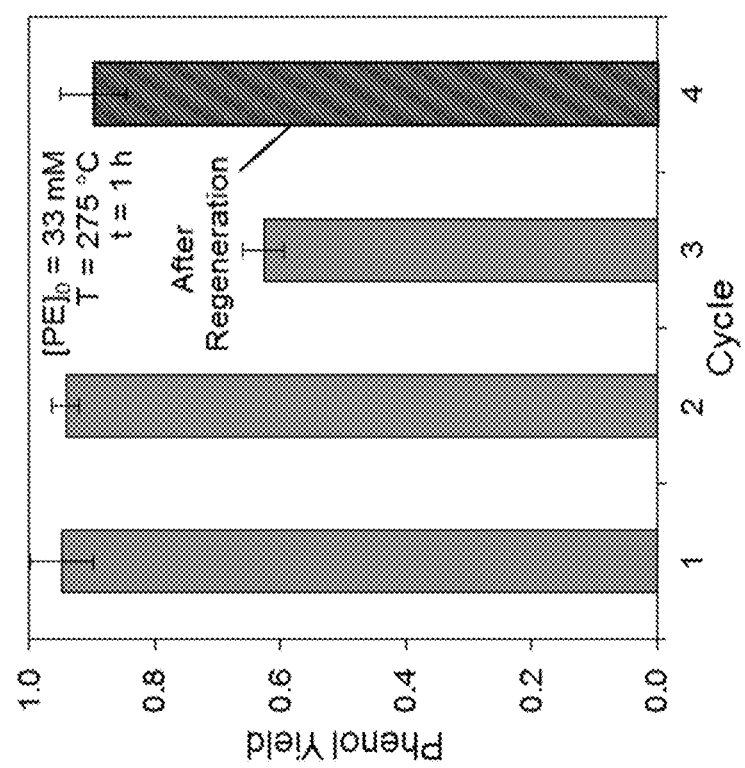
FIG. 22 shows the results of recycle and regeneration of Ni-HTC-rh catalyst, with regeneration by calcination, rehydration, and redeposition of nitrate after cycle 3, according to exemplary embodiments of the present invention. The regeneration protocol includes calcining at 450° C., rehydrating, and redepositing of $Ni(NO_3)_2$ as an ethanolic solution, as described in the experimental section.
Figure 23:
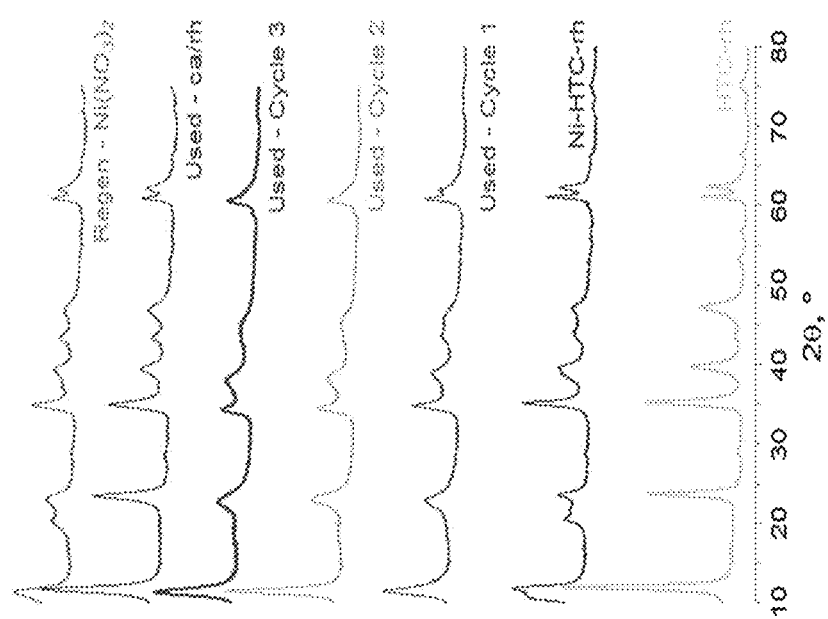
FIG. 23 summarizes XRD traces for fresh, recycled, and regenerated catalysts, according to exemplary embodiments of the present invention.

As demonstrated in FIG. 22, the catalyst activity of the Ni-HTC-rh is maintained through two cycles, after which activity decreases. The loss in activity is accompanied by a loss of the nitrate-intercalated domains and a partial loss of the HTC structure, as shown by XRD (see FIG. 23). Attempts to restore the HTC structure and $NO_3^-$ by direct rehydration and direct ion exchange of the used catalyst were unsuccessful, possibly due to a minor amount of carbonaceous material deposited on the catalyst surface. However, calcining the catalyst to fully produce the mixed oxide state and remove any carbonaceous deposits, followed by rehydration and redeposition of an ethanolic $Ni(NO_3)_2$ solution restored catalyst activity. The regeneration protocol is described in the experimental section below, but has not been optimized.

Whole Lignin

The activity of nitrate-intercalated HTC catalysts toward two process-relevant lignin streams—a deacetylated, disk-refined, enzymatically-hydrolyzed lignin from corn stover (DDE lignin) and a dilute acid-pretreated lignin from corn stover (DAP lignin)—was examined. Each of these streams was evaluated in four catalytic scenarios (no catalyst, HTC-rh, Ni-HTC-rh, and HTC-as($NO_3$), and in two solvents: $H_2O$ and 3M3P. While $H_2O$ was found above to not be optimal for β-O-4 bond cleavage in the model dimer PE, aqueous lignin depolymerization over HTC to facilitate integration into upstream and downstream biorefining processes was nonetheless examined.

Figure 24:
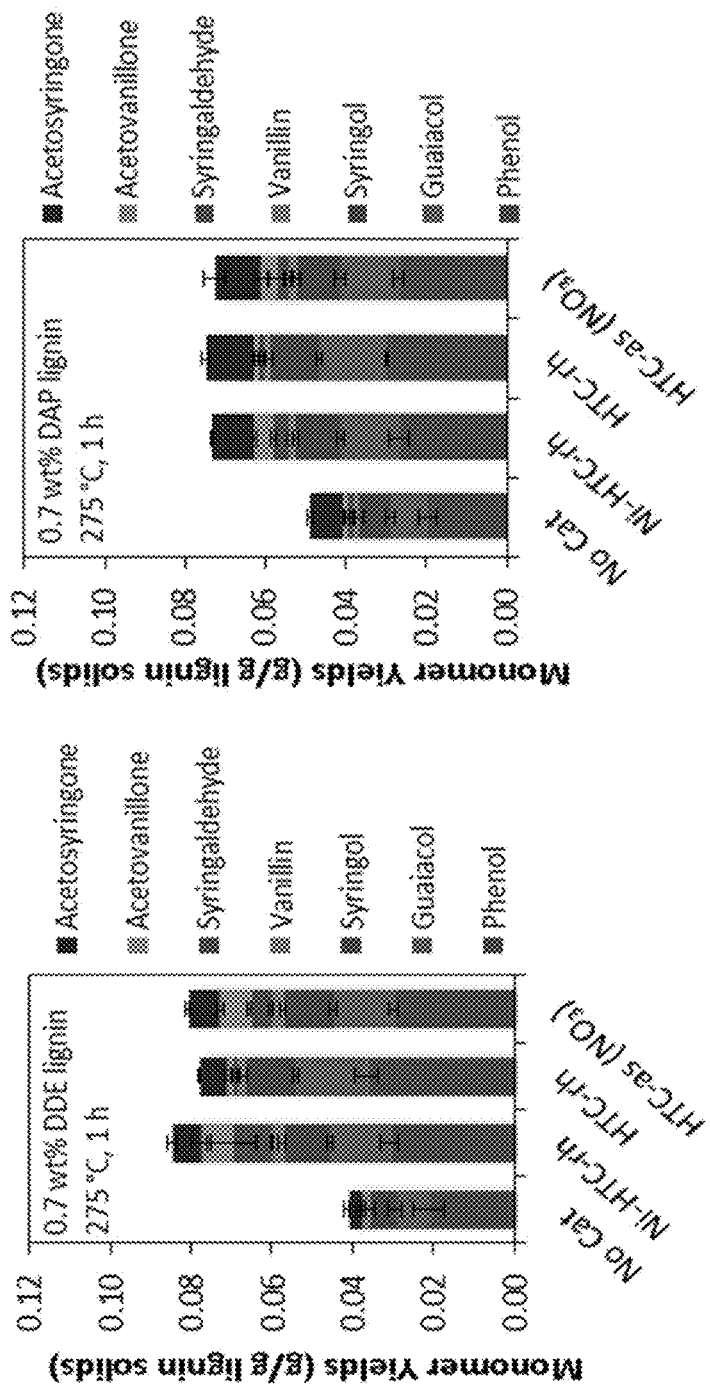
FIG. 24 shows yields of DCM-extracted monomers from DDE and DAP lignins reacted over HTC catalysts in $H_2O$ solvent.

The main detected monomeric products from both DAP and DDE lignins in $H_2O$ were phenol, guaiacol, and syringol, with smaller amounts of the analogous acyl ketones (acetosyringone and acetovanillone) and even smaller amounts of the analogous aldehydes (syringaldehyde and vanillin). In total, monomer yields detected by GC were 3.5-4.5% without catalyst and about 7% with catalyst, referenced to the lignin mass content in the feedstock, as shown in FIG. 24.

Figure 25:
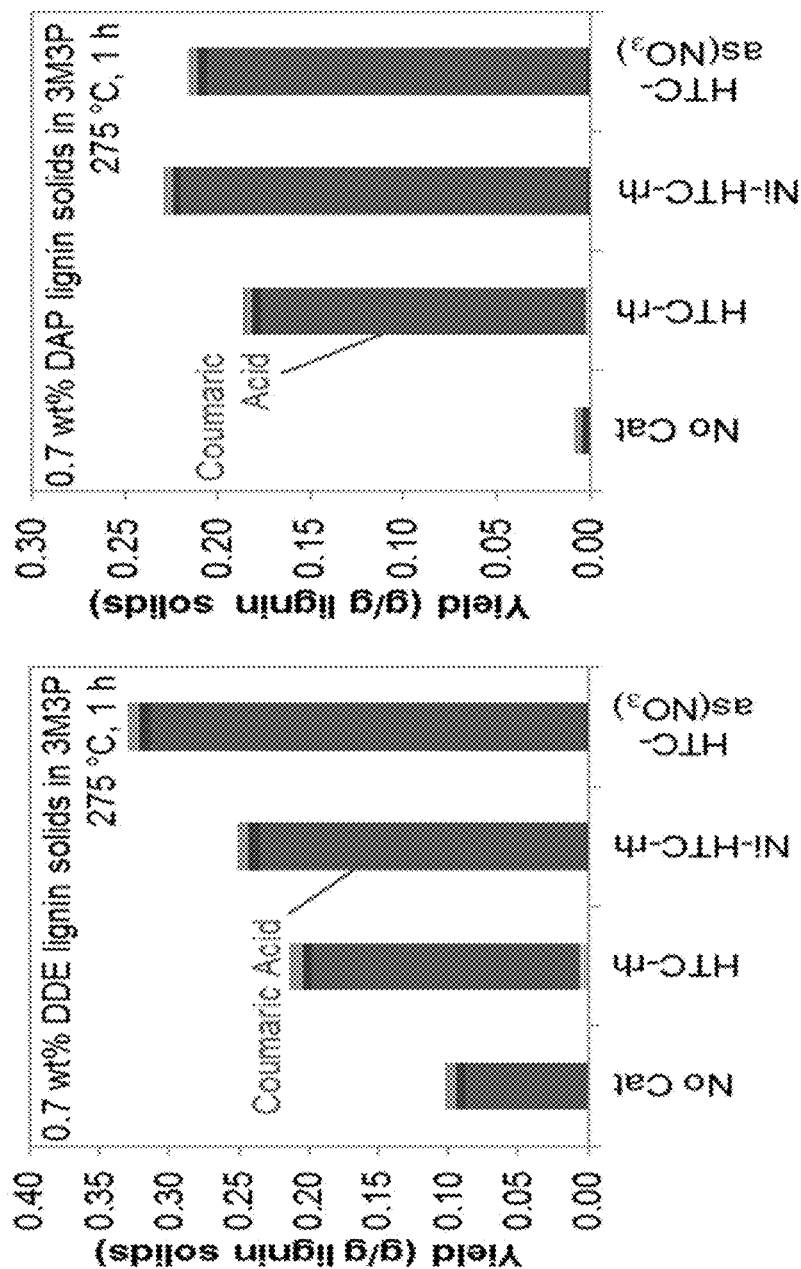
FIG. 25 shows monomer yields from DDE and DAP lignins over HTC catalysts in 3M3P solvent.

In contrast, the major product in 3M3P was a coumaric acid derivative. Minor products included guaiacol, syringol, 4-ethyl-phenol, 4-vinyl guaiacol, isoeugenol, acetovanillone, and allyl syringol. Total monomer yields were 10-15 wt % from DAP lignin and 8-12 wt % from DDE lignin, of which at least 88% was coumaric acid over the HTC catalysts, as shown in FIG. 25.

Figure 26:
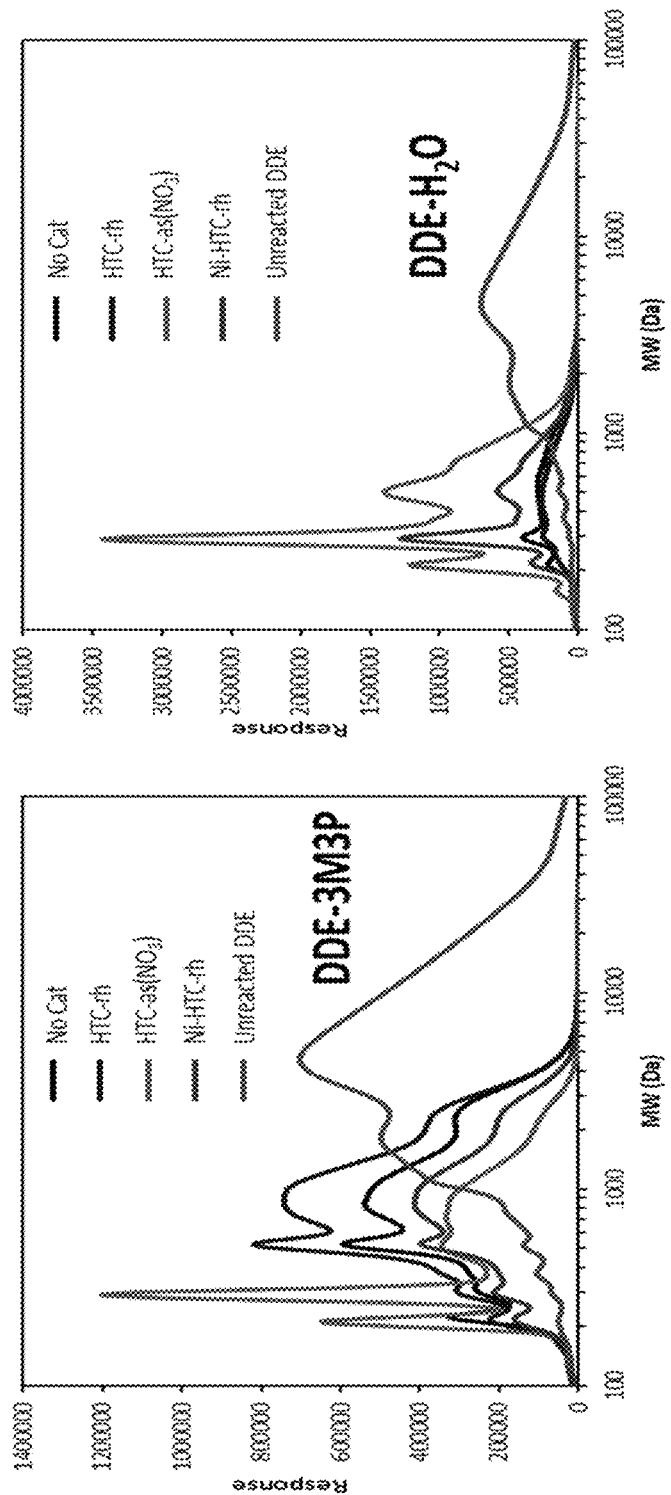
FIG. 26 shows gel permeation chromatography (GPC) traces for the THF-soluble portion of DDE lignin before and after reaction in 3M3P and $H_2O$ solvents.
Figure 27:
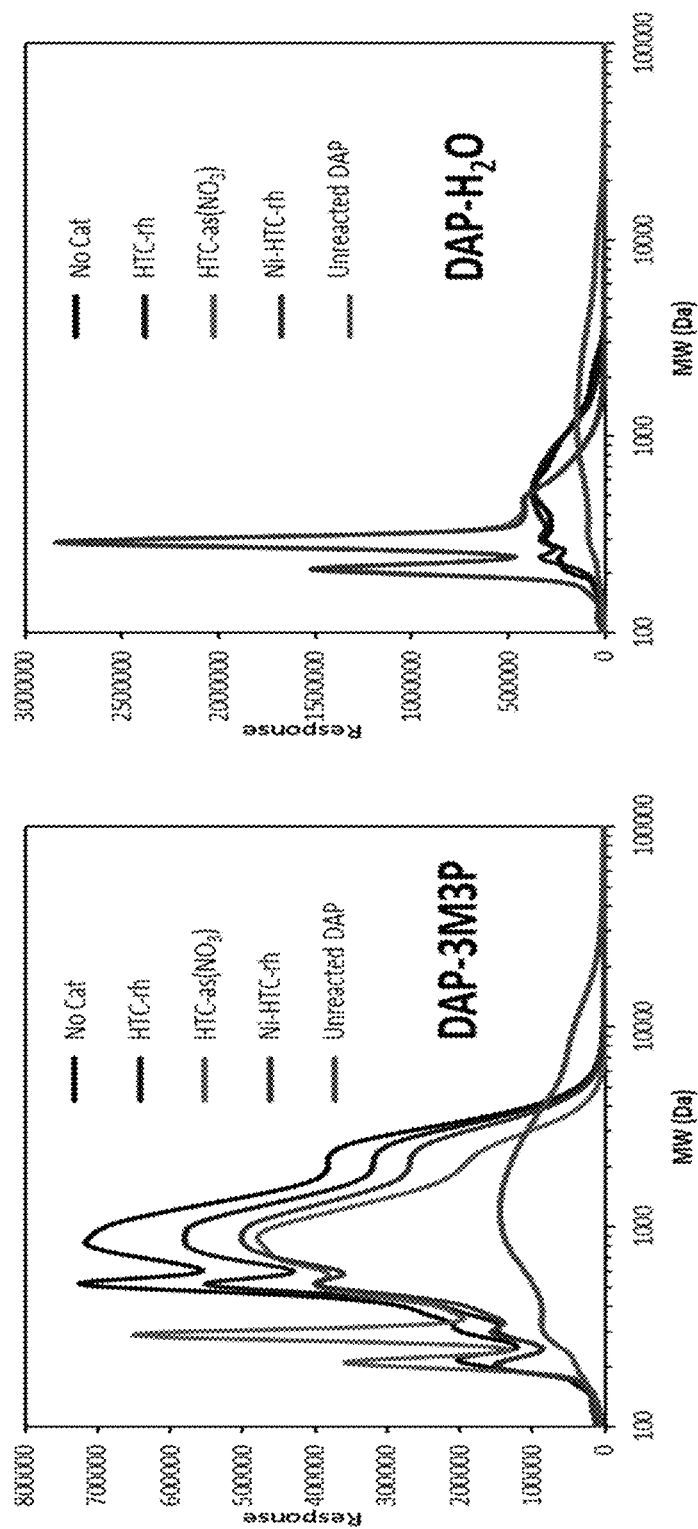
FIG. 27 shows GPC traces for the THF-soluble portion of DAP lignin before and after reaction in 3M3P and $H_2O$ solvents.

Monomers quantified by GC likely represent only a fraction of total monomers, at least for the aqueous samples. Gel Permeation Chromatography (GPC) suggests that a fraction much larger than 7% is converted into species with molecular weights of 200-300 Da, as shown in FIG. 26 for DDE lignin and in FIG. 27 for DAP lignins.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

What is claimed is:

1. A method for treating lignin, the method comprising contacting the lignin with a layered double hydroxide (LDH) catalyst comprising a nitrate anion, wherein the contacting depolymerizes the lignin resulting in a mixture comprising an aromatic compound.

2. The method of claim 1, wherein the aromatic compound comprises at least one of p-coumaryl alcohol, coniferyl alcohol, or sinapyl alcohol.

3. The method of claim 1, wherein the contacting is carried out in a solvent.

4. The method of claim 3, wherein the solvent comprises at least one of water, an alkane, an alcohol, or a ketone.

5. The method of claim 4, wherein the solvent comprises at least one of water, methanol, ethanol, propanol, isopropanol, acetone, methyl isobutyl ketone, heptane, tert-butanol, 2-ethyl-1-hexanol, or 3-methyl-3-pentanol.

6. The method of claim 1, wherein the LDH comprises hydrotalcite.

7. The method of claim 6, wherein the LDH has a metal counter ion comprising at least one of nickel, chromium, manganese, cobalt, copper, zinc, or gallium.

8. The method of claim 7, wherein the nitrate anion and the metal counter ion are associated with the LDH as at least one metal salt.

9. The method of claim 7, wherein the metal counter ion is present in the LDH at a concentration between about 5 wt % and about 15 wt %.

10. The method of claim 6, wherein the LDH has a concentration of basic sites between about 0.1 mmol hydroxide anions per gram of the LDH on a wet basis and about 2.0 mmol hydroxide anions per gram of the LDH on a wet basis.

11. The method of claim 6, wherein the LDH further comprises $Ni(OH)_2$.

12. The method of claim 1, further comprising, prior to the contacting, separating the lignin from a biomass feedstock comprising the lignin, a cellulose, and a hemicellulose.

13. The method of claim 12, wherein the separating is by a Kraft process.

14. The method of claim 1, wherein the contacting is performed at a temperature between about 150° C. and about 300° C.

15. The method of claim 1, wherein the contacting is maintained for a period of time between about 1 minute and about 8 hours.

16. The method of claim 1, further comprising separating the aromatic compound from the mixture.

17. The method of claim 16, wherein the separating is performed by at least one of a chromatographic method, electrophoresis, solvent extraction, filtration, centrifugation, isoelectric focusing, or HPLC.

18. The method of claim 17, wherein the chromatographic method comprises at least one of affinity chromatography, ion exchange chromatography, hydrophobic interaction chromatography, gel filtration chromatography, reverse phase chromatography, chromatofocusing, or differential solubilization.

* * * * *